US011839682B2

(12) United States Patent
Durany Turk et al.

(10) Patent No.: US 11,839,682 B2
(45) Date of Patent: Dec. 12, 2023

(54) IMAC-ENRICHED MICROALGAL CULTURE SUPERNATANT AND USES THEREOF

(71) Applicant: GAT BIOSCIENCES, S.L., Barcelona (ES)

(72) Inventors: Olga Durany Turk, Barcelona (ES); Jordi Segura De Yebra, Barcelona (ES); Jaume Mercade Roca, Barcelona (ES); Maria Teresa Lopez Cerro, Barcelona (ES); Cristina Lopez Paz, Barcelona (ES)

(73) Assignee: GAT BIOSCIENCES, S.L., Barcelona (ES)

( * ) Notice: Subject to any disclaimer, the term of this patent is extended or adjusted under 35 U.S.C. 154(b) by 2 days.

(21) Appl. No.: 17/053,471

(22) PCT Filed: May 8, 2019

(86) PCT No.: PCT/EP2019/061851
§ 371 (c)(1),
(2) Date: Nov. 6, 2020

(87) PCT Pub. No.: WO2019/215246
PCT Pub. Date: Nov. 14, 2019

(65) Prior Publication Data
US 2021/0228473 A1    Jul. 29, 2021

(30) Foreign Application Priority Data
May 8, 2018   (EP) ..................................... 18382314

(51) Int. Cl.
A61K 8/99      (2017.01)
A61K 8/64      (2006.01)
A61Q 19/08     (2006.01)

(52) U.S. Cl.
CPC .................. *A61K 8/99* (2013.01); *A61K 8/64* (2013.01); *A61Q 19/08* (2013.01)

(58) Field of Classification Search
CPC ....................................................... A61Q 19/08
See application file for complete search history.

(56) References Cited

U.S. PATENT DOCUMENTS 8,927,522 B2   1/2015   Coragliotti et al.

FOREIGN PATENT DOCUMENTS

| EP | 1402898 A1 | 3/2004 | |
|----|------------|--------|--|
| EP | 1437124 B1 * | 3/2008 | ............ A61K 8/19 |
| EP | 2875805 A1 | 5/2015 | |
| EP | 2646115 B1 | 11/2017 | |
| FR | 2785910 A1 | 5/2000 | |
| FR | 2785910 A1 * | 6/2002 | ............ A61K 36/04 |
| KR | 20170090690 A * | 8/2017 | ............ A61K 31/185 |
| WO | 2009141164 A1 | 11/2009 | |
| WO | 2016166047 A1 | 10/2016 | |

OTHER PUBLICATIONS

Yun-Hee Choi et al, Mycosporine-Like Amino Acids Promote Wound Healing through Focal Adhesion Kinase (FAK) and Mitogen-Activated Protein Kinases (MAP Kinases) Signaling Pathway in Keratinocytes, Mar. Drugs 2015, 13, 7055-7066 (Year: 2015).*
John J. Lee, The taxonomic identity and physiological ecology of *Chlamydomonas hedleyi* sp. nov., algal flagellate symbiont from the foraminifer Archaias angulatus. British Phycological Journal 9(4): 407-422, 1974 (Year: 1974).*
Suh SS, Hwang J, Park M, Seo HH, Kim HS, Lee JH, Moh SH, Lee TK. Anti-inflammation activities of mycosporine-like amino acids (MAAs) in response to UV radiation suggest potential anti-skin aging activity. Mar Drugs. Oct. 14, 2014;12(10):5174-87. doi: 10.3390/md12105174. PMID: 25317535; PMCID: PMC4210892 (Year: 2014).*
Mushir, S.; Fatma, T. Ultraviolet Radiation-absorbing Mycosporine-like Amino Acids in Cyanobacterium Aulosira fertilissima: Environmental Perspective and Characterization. Curr. Res. J. Biol. Sci. 2011, 3, 165-171 (Year: 2011).*
KR20170090690A, Korean Intellectual Property Office Translation, downloaded in Jul. 2022 (Year: 2022).*
EP1437124B1, Google English Translation, downloaded in Jul. 2022 (Year: 2022).*
Hongxia Wang et al, The Global Phosphoproteome of Chlamydomonas reinhardtii Reveals Complex Organellar Phosphorylation in the Flagella and Thylakoid Membrane, Molecular & Cellular Proteomics 13.9, 2014 (Year: 2014).*
FR2785910A1, Google English Translation, downloaded in Jul. 2022 (Year: 2022).*
Choi et al., "Mycosporine-Like Amino Acids Promote Wound Healing Through Focal Adhesion Kinase (FAK) and Mitogen-Activated Protein Kinases (Map Kinases) Signaling Pathway in Keratinocytes", Choi et al., Mar. Drugs, vol. 13, No. 12, pp. 7055-7066, 2015.
Hardwicke et al., Epidermal Growth Factor Therapy and Wound Healing Past, Present and Future Perspectives, Surgeon, vol. 6, No. 3, pp. 172-177, 2008.
Wang et al, "The Global Phosphoproteome of Chlamydomonas Reinhardtii Reveals Complex Organellar Phosphorylation in the Flagella and Thylakoid Membrane", Molecular Cellular Proteomics, vol. 13, No. 9, pp. 2337-2353, 2014.
Castaldo et al., "A Fast and Easy Strategy for Protein Purification Using Teabags", Scientific Reports, vol. 6, pp. 1-4, 2016.
Apone et al, "A Mixture of Peptides and Sugars Derived From Plant Cell Walls Increases Plant Defense Responses To Stress and Attenuates Ageing-Associated Molecular Changes in Cultured Skin Cells", Journal of Biotechnology, vol. 145, No. 4, pp. 367-376, 2010.
Du et al., "Skin Health Promotion Effects of Natural Beta-Glucan Derived From Cereals and Microorganisms: A Review", Phytotherapy Research, vol. 28, No. 2, pp. 159-166, 2014.

(Continued)

*Primary Examiner* — Mark V Stevens
*Assistant Examiner* — Alparslan Asan
(74) *Attorney, Agent, or Firm* — LUCAS & MERCANTI, LLP

(57) ABSTRACT

A method for obtaining a culture supernatant form microalgae is provided, particularly wherein the culture supernatant is IMAC-enriched microalga culture supernatant and to an IMAC-enriched microalga culture supernatant obtained by the method of the invention. Also provided is a combination having a microalgal culture supernatant and a growth factor and to a cell culture media; a cosmetic composition and pharmaceutical composition and uses thereof.

17 Claims, 5 Drawing Sheets

(56) References Cited

OTHER PUBLICATIONS

Kinoshita et al., "Primary Structure and Expression of a Gamete Lytic Enzyme in Chlamydomonas Reinhardtii: Similarity of Functional Domains to Matrix Metalloproteases", Proc. Natl. Acad. Sci. USA, vol. 89, No. 10, pp. 4693-4697, 1992.
Neupert et al., "Generation of Chlamydomonas Strains That Efficiently Express Nuclear Transgenes", The Plant Journal, vol. 57, No. 6, pp. 1140-1150, 2009.
International Search Report and Written Opinion for Corresponding International Application No. PCT/EP2019/061851 (11 Pages) (dated Jun. 18, 2019).
International Preliminary Report on Patentability for Corresponding International Application No. PCT/EP2019/061851 (9 Pages) (dated Nov. 10, 2020).

\* cited by examiner

B

A 0.5%FBS  0.5%FBS+MS  0.5%FBS+EGF  10 %FBS

B

IMAC-ENRICHED MICROALGAL CULTURE SUPERNATANT AND USES THEREOF

CROSS REFERENCE TO RELATED APPLICATION

This Application is a 371 of PCT/EP2019/061851 filed on May 8, 2019 which, in turn, claimed the priority of European Patent Application No. 18382314.5 filed on May 8, 2018, both applications are incorporated herein by reference.

FIELD OF THE INVENTION

The invention relates to a microalgal culture supernatant, methods for obtaining the same and uses of microalgal culture supernatant in cosmetic and therapeutic treatments.

BACKGROUND OF THE INVENTION

Skin aging is a worldwide concern caused by intrinsic changes and extrinsic damages that result in visible effects such as wrinkling, sagging, increased laxity and loss of moisture. At the cellular and molecular level skin changes associated with aging are manifested as a reduction in the extracellular matrix components (ECM) caused by both a decreased proliferative capacity of skin derived cells (fibroblasts) and increased expression of enzymes that degrade the collagenous matrix. Collagen, elastin, fibronectin, proteoglycans, glycosaminoglycans, and matricellular proteins, are all ECM components that are decreased, damaged or have altered expression with aging and stress.

Polysaccharides and glycoproteins play a fundamental structural role by forming a matrix to support all the cells in the dermis. The role of ECM components, however, is not only limited to be a physical support but is also to regulate the activity and fate of cells that surround them by influencing their proliferation, development, and metabolic activity. Several studies have reported that different ECM components have varied effects on fibroblast proliferation, migration, differentiation into myofibroblasts and collagen production. Among the diverse components of the ECM, growth factors are regulatory secreted proteins that acts as chemical messengers by attaching to cell receptors to propagate inter and intracellular signaling pathways that may control cell growth, proliferation, and differentiation. In the skin, GFs are synthesized by all cells of the dermis and epidermis and its role in the formation of ECM and control of other GF has converted those on important targets of research in the field of skin wound healing and cosmetic applications.

Cosmetic industry is continuously looking for effective and natural components to improve skin appearance and delay effects of skin aging. Currently, several cosmetic products in the market intended for skin rejuvenation contain growth factors to promote collagen and elastin synthesis. The use of glycoproteins, polysaccharides, peptides extracts and growth factors in cosmetics has been proved to provide beneficial effects on skin care and wound healing (Apone et al. 2010 J Biotechnol 145:367-376) (Du et al. 2014 Phyther Res 28:159-166). Several growth factors used in cosmetic products are recombinantly produced in other organisms most commonly bacteria such as *E. coli*.

Many efforts have been taken to discover natural products that restore ECM and skin cells. One of these components is collagen, a glycoprotein with an unusual amino acid composition rich in proline and hydroxyproline. Collagen, sometimes in combination with other glycopeptides, is used in cosmetics to treat wrinkles and other unaesthetic blemishes by improving skin hydration and elasticity. Despite its many advantages, one of the main drawbacks of collagen use in cosmetics, or its hydrolysates, comes from its frequent animal origin and the risk associated with virus and toxins contamination.

A mixture of isolated polysaccharides from microalgae of the species *Parachlorella kessleri* or *Parachlorella beijerinckii* has been described in U.S. Pat. No. 8,927,522B2 for use as topical personal care products, cosmetics, and wrinkle reduction compositions.

Exopolysaccharides from the marine *Pseudoalteromonas* s.p bacteria have also been proposed in EP 2646115 B1 as an alternative to hyaluronic acid, that is used to even out the skin surface and treat problems caused by poor hydration of the skin, mucous membranes, hair and/or nails. Similarly, the role of a *Pseudoalteromonas antartica* glycoprotein, Antarticine-NF3, has been reported in EP1402898B1 to improve the adhesion of human dermal fibroblasts and promote the cellular growth of human epidermal keratinocytes but no stimulation of fibroblast, producers of collagen and ECM was reported. Another example is a purified fungal glycoprotein which has a stimulatory effect on keratinocyte cell regeneration as disclosed in EP2875805B1.

Due to the huge demand in the cosmetic industry to find a natural, safe, animal free anti-aging ingredient there is a need to develop new molecules that prevent or delay skin aging.

SUMMARY OF THE INVENTION

The authors of the present invention have observed that molecules naturally secreted by microalgae have a potent stimulatory activity on the proliferation and structural organization of fibroblasts. These molecules may be purified by a method that does not require harsh or chemical steps that may add costs or toxicity to the ingredient (or activator). In addition, the inventors have shown that the combination of microalgal culture supernatants and recombinant epidermal growth factor (EGF) results in a synergistic effect on the proliferation and structural organization of fibroblasts. All these findings indicate that the use of microalgal culture supernatant alone or in combination with growth factors may be applicable to those treatments/therapies and media cultures currently using growth factors to enhance its effectiveness. The present invention describes a new component to treat and improve skin care and to use as a booster of fibroblast activity. Additional advantages over current plant extracts are simplicity (no cell wall preparations and purifications are required), low cost of obtention of the product and high presence of glycoproteins rich in hydroxyproline, an important component of collagen.

In a first aspect, the invention relates to a cosmetic method for skin care which comprises administration to a subject of a cosmetic composition or cosmeceutical comprising a cosmetically acceptable adjuvant and
  (i) a microalgal culture supernatant obtained by a method comprising the steps of:
    a) culturing microalgae belonging to Chlorophyceae class or Volvocales order under conditions suitable for the growth of the microalgae and for the secretion of molecules to the culture medium, and
    b) obtaining a microalgal culture supernatant by removing cells from the culture of step a), (ii) an IMAC-enriched microalgal culture supernatant obtained by a method comprising the steps of
  a) culturing microalgae under conditions suitable for the growth of the microalgae and for the secretion of molecules to the culture medium,
  b) obtaining a microalgal culture supernatant by removing cells from the culture of step a),
  c) incubating the microalgal culture supernatant from step b) with a metal affinity chromatography resin under conditions allowing the binding of those molecules in the supernatant showing affinity to the resin,
  d) separating the molecules that bind to the metal affinity chromatography resin from those that do not so bind and
  e) eluting from the resin those molecules that bind to the resin, thereby obtaining an IMAC-enriched microalga culture supernatant, or a
(iii) a combination comprising a growth factor, and a microalgal culture supernatant as defined in (i) or an IMAC-enriched microalgal culture supernatant as defined in (ii).

In a second aspect, the invention relates to a cosmetic method for a condition which requires increased proliferation of fibroblasts which comprises administration to a subject of a cosmetic composition or cosmeceutical comprising a cosmetically acceptable adjuvant and
  (i) a microalgal culture supernatant obtained by a method comprising the steps of:
    a) culturing microalgae belonging to Chlorophyceae class or Volvocales order under conditions suitable for the growth of the microalgae and for the secretion of molecules to the culture medium, and
    b) obtaining a microalgal culture supernatant by removing cells from the culture of step a),
  (ii) an IMAC-enriched microalgal culture supernatant obtained by a method comprising the steps of
    a) culturing microalgae under conditions suitable for the growth of the microalgae and for the secretion of molecules to the culture medium,
    b) obtaining a microalgal culture supernatant by removing cells from the culture of step a),
    c) incubating the microalgal culture supernatant from step b) with a metal affinity chromatography resin under conditions allowing the binding of those molecules in the supernatant showing affinity to the resin,
    d) separating the molecules that bind to the metal affinity chromatography resin from those that do not so bind and
    e) eluting from the resin those molecules that bind to the resin, thereby obtaining an IMAC-enriched microalga culture supernatant, or a
  (iii) a combination comprising a growth factor, and a microalgal culture supernatant as defined in (i) or an IMAC-enriched microalgal culture supernatant as defined in (ii), and wherein the method is performed in the presence of reduced amounts of fetal serum or growth factors.

In a third aspect, the invention relates to a cosmetic composition or cosmeceutical comprising a cosmetically acceptable adjuvant and
  (i) a microalgal culture supernatant obtained by a method comprising the steps of:
    a) culturing microalgae belonging to Chlorophyceae class or Volvocales order under conditions suitable for the growth of the microalgae and for the secretion of molecules to the culture medium, and
    b) obtaining a microalgal culture supernatant by removing cells from the culture of step a),
  (ii) an IMAC-enriched microalgal culture supernatant obtained by a method comprising the steps of
    a) culturing microalgae under conditions suitable for the growth of the microalga and for the secretion of molecules to the culture medium,
    b) obtaining a microalgal culture supernatant by removing cells from the culture of step a),
    c) incubating the microalgal culture supernatant from step b) with a metal affinity chromatography resin under conditions allowing the binding of molecules to the resin of those molecules in the supernatant which show affinity to the resin,
    d) separating the molecules that bind to the metal affinity chromatography resin from those that do not so bind and
    e) eluting from the resin those molecules that bind to the resin, thereby obtaining an IMAC-enriched microalgal culture supernatant, or
  (iii) a combination comprising a growth factor, and a microalgal culture supernatant as defined in (i) or an IMAC-enriched microalgal culture supernatant as defined in (ii).

In a fourth aspect, the invention relates to a pharmaceutical composition comprising a pharmaceutically acceptable adjuvant and
  (i) a microalgal culture supernatant obtained by a method comprising the steps of:
    a) culturing microalgae belonging to Chlorophyceae class or Volvocales order under conditions suitable for the growth of the microalgae and for the secretion of molecules to the culture medium, and
    b) obtaining a microalgal culture supernatant by removing cells from the culture of step a),
  (ii) an IMAC-enriched microalgal culture supernatant obtained by a method comprising the steps of
    a) culturing microalgae under conditions suitable for the growth of the microalgae and for the secretion of molecules to the culture medium,
    b) obtaining a microalgal culture supernatant by removing cells from the culture of step a),
    c) incubating the microalgal culture supernatant from step b) with a metal affinity chromatography resin under conditions allowing the binding of molecules to the resin of those molecules in the supernatant which show affinity to the resin,
    d) separating the molecules that bind to the metal affinity chromatography resin from those that do not so bind and
    e) eluting from the resin those molecules that bind to the resin, thereby obtaining an IMAC-enriched microalga culture supernatant, or
  (iii) a combination comprising a growth factor, and a microalgal culture supernatant as defined in (i) or an IMAC-enriched microalgal culture supernatant as defined in (ii)
for use in wound healing or for repairing skin damage.

In a fifth aspect, the invention relates to a pharmaceutical composition comprising a pharmaceutically acceptable adjuvant and
  (i) a microalgal culture supernatant obtained by a method comprising the steps of:
    a) culturing microalgae belonging to Chlorophyceae class or Volvocales order under conditions suitable for the growth of the microalgae and for the secretion of molecules to the culture medium, and
b) obtaining a microalgal culture supernatant by removing cells from the culture of step a),
(ii) an IMAC-enriched microalgal culture supernatant obtained by a method comprising the steps of
a) culturing microalgae under conditions suitable for the growth of the microalgae and for the secretion of molecules to the culture medium,
b) obtaining a microalgal culture supernatant by removing cells from the culture of step a),
c) incubating the microalgal culture supernatant from step b) with a metal affinity chromatography resin under conditions allowing the binding of molecules to the resin of those molecules in the supernatant which show affinity to the resin,
d) separating the molecules that bind to the metal affinity chromatography resin from those that do not so bind and
e) eluting from the resin those molecules that bind to the resin, thereby obtaining an IMAC-enriched microalga culture supernatant, or
(iii) a combination comprising a growth factor, and a microalgal culture supernatant as defined in (i) or an IMAC-enriched microalgal culture supernatant as defined in (ii)

for use in the prevention and/or treatment of a disease or condition which requires increased proliferation of fibroblast and wherein said treatment is performed in the presence of reduced levels of serum or growth factors.

In a sixth aspect, the invention relates to a pharmaceutical composition comprising a pharmaceutically acceptable adjuvant and
(i) a microalgal culture supernatant obtained by a method comprising the steps of:
a) culturing microalgae belonging to Chlorophyceae class or Volvocales order under conditions suitable for the growth of the microalgae and for the secretion of molecules to the culture medium, and
b) obtaining a microalgal culture supernatant by removing cells from the culture of step a),
(ii) an IMAC-enriched microalgal culture supernatant obtained by a method comprising the steps of
a) culturing microalgae under conditions suitable for the growth of the microalgae and for the secretion of molecules to the culture medium,
b) obtaining a microalgal culture supernatant by removing cells from the culture of step a),
c) incubating the microalgal culture supernatant from step b) with a metal affinity chromatography resin under conditions allowing the binding of molecules to the resin of those molecules in the supernatant which bind to the resin,
d) separating the molecules that bind to the metal affinity chromatography resin from those that do not so bind and
e) eluting from the resin those molecules that bind to the resin, thereby obtaining an IMAC-enriched microalga culture supernatant or
(iii) a combination comprising a growth factor, and a microalgal culture supernatant as defined in (i) or an IMAC-enriched microalgal culture supernatant as defined in (ii).

In a seventh aspect, the invention relates to a combination comprising a growth factor and
(i) a microalgal culture supernatant obtained by a method comprising the steps of:
a) culturing microalgae under conditions suitable for the growth of the microalgae and for the secretion of molecules to the culture medium, and
b) obtaining a microalgal culture supernatant by removing cells from the culture of step a), or
(ii) an IMAC-enriched microalgal culture supernatant obtained by a method comprising the steps of
a) culturing microalgae under conditions suitable for the growth of the microalgae and for the secretion of molecules to the culture medium,
b) obtaining a microalgal culture supernatant by removing cells from the culture of step a),
c) incubating the microalgal culture supernatant from step b) with a metal affinity chromatography resin under conditions allowing the binding of histidine-rich molecules to the resin,
d) separating the molecules that bind to the metal affinity chromatography resin from those that do not so bind and
eluting from the resin those molecules that bind to the resin, thereby obtaining an IMAC-enriched microalgal culture supernatant.

In an eight aspect, the invention relates to a cell culture media comprising
(i) a microalgal culture supernatant obtained by a method comprising the steps of:
a) culturing microalgae under conditions suitable for the growth of the microalgae and for the secretion of molecules to the culture medium, and
b) obtaining a microalgal culture supernatant by removing cells from the culture of step a), or
(ii) an IMAC-enriched microalgal culture supernatant obtained by a method comprising the steps of
a) culturing microalgae under conditions suitable for the growth of the microalgae and for the secretion of molecules to the culture medium,
b) obtaining a microalgal culture supernatant by removing cells from the culture of step a),
c) incubating the microalgal culture supernatant from step b) with a metal affinity chromatography resin under conditions allowing the binding of molecules to the resin of those molecules which show affinity towards the resin,
d) separating the molecules that bind to the metal affinity chromatography resin from those that do not so bind and
e) eluting from the resin those molecules that bind to the resin, thereby obtaining an IMAC-enriched microalga culture supernatant,
or a combination of the invention.

In a ninth aspect, the invention relates to a method for obtaining a microalgal culture supernatant from a microalga comprising the steps of:
a) culturing the microalga belonging to Chlorophyceae class or Volvocales order under conditions suitable for the growth of the microalga and for the secretion of molecules to the culture medium, and
b) obtaining a microalgal culture supernatant by removing cells from the culture of step a).

In a tenth aspect, the invention relates to a microalga culture supernatant obtained by the method of the invention.

In an eleventh aspect, the invention relates to a combination comprising a microalga culture supernatant according the invention and a growth factor.

In a twelfth aspect, the invention relates to an vitro method for inducing fibroblasts proliferation which comprises contacting a preparation comprising fibroblast with a microalgae culture supernatant according to the invention in the presence of reduced amounts of fetal serum or growth factor.

DETAILED DESCRIPTION OF THE INVENTION

Figure 1:
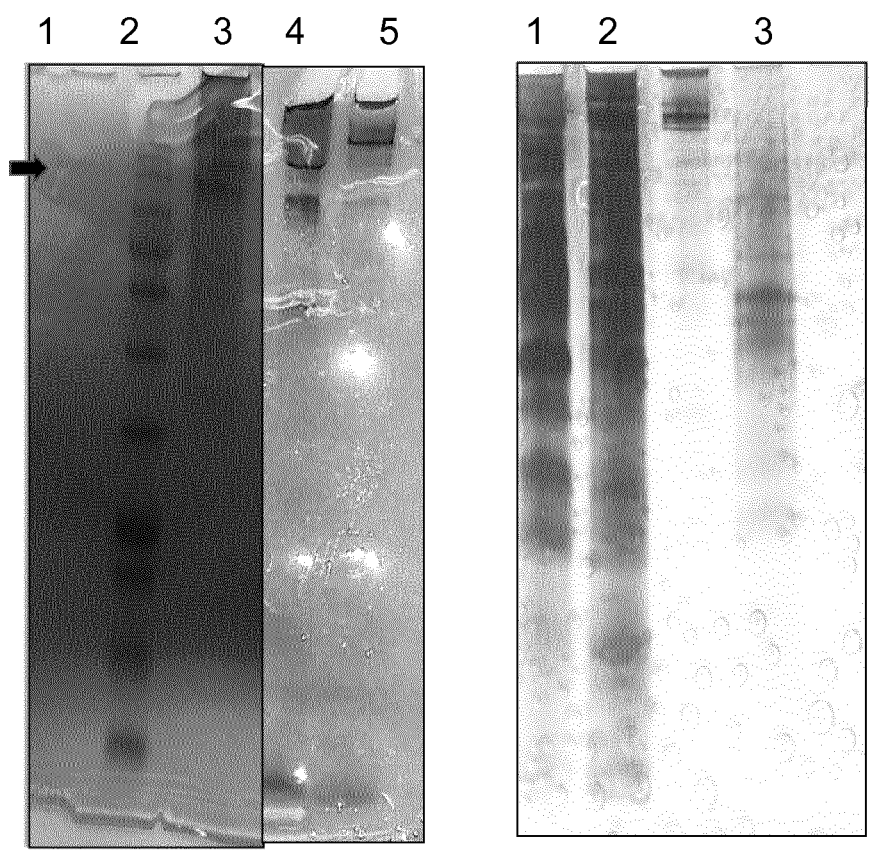
FIG. 1. Identification of glycoproteins and IMAC enriched proteins from *Chlamydomonas* media A) Identification of glycoproteins by SDS PAGE and PAS staining. Lanel: IMAC enriched glycoprotein (arrow indicates a glycoprotein at approximately ~150 kDa), 2: Protein molecular weight marker, 3: Microalgal culture supernatant concentrated by tangential flow filtration (Cut off membrane 10 kDa); 4 and 5; Microalgal culture supernatant concentrated by lyophilization followed by dyalisis. B) Silver staining identification of secreted proteins obtained by concentration and lyophilization (lanes 1 and 2) or IMAC purification (lane 3).

The inventors have identified a microalgal culture supernatant containing components that are naturally secreted by microalgae and have characterized its use alone or in combination with a recombinant growth factor (GF) as a treatment for the skin, hair, nails or mucous membranes. They have observed that these microalgal culture supernatants have a potent effect on the proliferation of fibroblasts and this effect acts synergistically with the action of epidermal growth factor, providing thus alternative and more effective cosmetic and therapeutic treatments for those conditions in which extracellular matrix and/or skin cells are decreased, damaged or altered.

Method for Obtaining a Microalgal Culture Supernatant of the Invention

In a first aspect, the invention relate to a method for obtaining a microalgal culture supernatant from a microalga comprising the steps of:
a) culturing the microalga belonging to Chlorophyceae class or Volvovovales order under conditions suitable for the growth of the microalga and for the secretion of molecules to the culture medium, and
b) obtaining a microalgal culture supernatant by removing cells from the culture of step a).

Microalgal culture supernatant as used herein relates to a product obtained from microalgae, for example, by subjecting a microalgae culture to specific treatments. In the context of the invention, the microalgal culture supernatant comprises different molecules, such as glycoproteins, proteins that contain oligosaccharide chains (glycans) covalently attached to amino acid side-chains. In a particular embodiment, the microalgal culture supernatant obtained by the method of the invention comprises glycoproteins.

"Glycoprotein" as used herein relates to proteins that contain oligosaccharide chains (glycans) covalently attached to amino acid side-chains.

Microalgae as used herein relates to large and diverse group of simple, typically autotrophic organisms, ranging from unicellular to multicellular forms, microscopic algae, typically found in freshwater and marine systems. Examples of suitable microalgae for obtaining a microalgal culture supernatant of the invention, include microalgae from the phylums Cyanophyta, Chlorophyta, Rhodophyta, Heterokontophyta, and Haptophyta. The algae from the phylum Cyanophyta can be *Spirulina* (Arthrospira), *Aphanizomenon flos-aquae*, *Anabaena cylindrica* or *Lyngbya majuscule*. The algae from the phylum Chlorophyta can be *Chlorella, Scenedesmus, Dunaliella, Tetraselmis, Haematococcus, Ulva, Codium, Caulerpa* spp or *Botryococcus braunii*. The algae from the phylum Rhodophyta can be *Porphyridium cruentum, Gracilaria* sp., *Grateloupia* sp, *Palmaria* sp. *Corallina* sp., *Chondrus crispus, Porphyra* sp. *or Rhodosorus* sp. The algae from the phylum Heterokontophyta can be *Nannochlorropsis oculata, Odontella aurita, Phaeodactylum tricornutum. Fucus* sp. *Sargassum* sp. *Padina* sp., *Undaria pinnatifida*, or *Laminaria* sp. The algae from the phylum Haptophyta can be *Isochrysis* sp. *Tisochrysis* sp. or *Pavlova* sp. The algae can be *Chrypthecodinium cohnii, Schizochytrium, Ulkenia* or *Euglena gracilis*. The algae can be a green microalga such as *Chlorella, Scenedesmus,*

*Dunialiella, Haematococcusand Bracteacoccus*; haptophyte microalgae such as *Isochrysis*; and heterokontophyta microalgae such as *Phaeodactylum, Ochromonas* and *Odontella*.

In a preferred embodiment, the microalgae is from Chlorophyceae class. In a more preferred embodiment, the the microalgae from Chlorophyceae class are from Volvovocales order. In another more preferred embodiment, the microalgae from Volvovocales order are from Chlamydomonadaceae family. In another more preferred embodiment, the microalgae from Chlamydomonadaceae family is from the genus *Chlamydomonas*.

In a particular embodiment, the microalga is a green alga. Suitable examples of green algae are *Chlorella* or *Haematyococcus* or *Chlamydomonas*.

*Chlamydomonas*, as used herein relates to a genus of green algae consisting of about 325 species all unicellular *flagellates*, found in stagnant water and on damp soil, in freshwater, seawater, and even in snow as "snow algae". In a more preferred embodiment, the microalga is *Chlamydomonas reinhardtii*.

*Chlamydomonas reinhardtii*, as used herein is a single-cell green alga about 10 micrometres in diameter that swims with two flagella. It has a cell wall made of hydroxyproline-rich glycoproteins, a large cup-shaped chloroplast, a large pyrenoid, and an "eyespot" that senses light.

The first step of the method of the invention comprises culturing the microalgae under conditions suitable for the growth of the microalga and for the secretion of molecules, as a way of example glycoproteins, to the culture medium.

In a preferred embodiment, the microalgae used in the method of the invention are cell wall-less microalgae. Cell wall-less microalgae include strains that are naturally devoid of cell wall due to a genetic defect as well as cell wall containing microalgae that have been treated so as to remove the cell wall.

A cell wall-less strain, as used herein relates to a microalgal strain lacking cell wall. Therefore, using a cell wall-less strain a higher amount of molecules, such as glycoproteins, may be obtained in the method of the invention. Illustrative non limitative examples of cell wall less strains that can be used according to the invention are UVM4, cw15 or C1883. UVM4 may be obtained from Neupert J. et al 2009 The plant journal 57, 1140-1150 and cw15 or C1883 from *Chlamydomonas* Resource Center. Illustrative non limitative examples of cell wall containing strains that can be used according to the invention are CC-124, 21 gr, CC-125, CC-1690 and CC-1691, all of them available from *Chlamydomonas* Resource Center.

The cell used in the methods of the invention is a cell, preferably a *Chlamydomonas reinhardtii* cell, expressing a protein comprising a poly-histidine tag, more particularly a hexa-histidine tag.

In case that a wild-type strain containing a cell wall is used, the cells can be treated so as to remove the cell wall. Methods for removing the cell wall from microalgae are well-known in the art and can be applied in the present invention. For instance, for the *Chlamydomonas reinhardtii*, the cell wall can be removed by treatment with the zinc-containing metallo-protease gametolysin as described by Kinoshita, T. (Proc. Natl. Acad. Sci. USA, 1992, 89, 4693-4697).

In a preferred embodiment, the microalgae used in the present invention belongs to a strain that has not been modified by the insertion of a heterologous gene or by the insertion of chimeric genes that comprise elements that, if present in the native genome of the strain, are found in a different order.

In another embodiment, the microalga used in the method of the invention is a mixotroph organism (i.e., an organism that can use a mix of different sources of energy and carbon).

Culture conditions suitable for the growth of the microalga and for the secretion of molecules, more particularly glycoproteins, to the culture medium may be different for each type of microalga. However, those conditions are known by skilled workers and are readily determined. Similarly, the duration of maintenance can differ with the microalgae and with the amount of different molecules from the culture supernatant desired to be prepared. Again, those conditions are well known and can readily be determined in specific situations.

In a particular embodiment, the microalga is grown under mixotrophic conditions. In a particular embodiment, the microalga is cultured until an $OD_{750\ nm}$ of 2.5.

In a particular embodiment, the microalga is cultured in a photobioreactor in a suitable medium, under a suitable luminous intensity, at a suitable temperature. Practically any medium suitable for growing microalgae can be used; nevertheless, illustrative, non-limitative examples of said media include TAP media. The luminous intensity can vary widely, nevertheless, in a particular embodiment, the luminous intensity is comprised between 25 and 150 μmol photons $m^{-2}\ s^{-1}$, particularly 100 μE. The temperature can vary usually between about 17° C. and about 30° C., particularly 25° C. The culture can be performed in the absence of aeration or with aeration. In a particular embodiment, the culture is carried out without aeration. In another particular embodiment, the culture is carried out with aeration. In a preferred embodiment, the conditions are maintained until reaching a stationary phase.

The second step of the method of the invention comprises obtaining a microalgal culture supernatant by removing cells from the culture of the first step.

In a preferred embodiment, the cells from the culture of step a) are removed by centrifugation. In another preferred embodiment, the cells from culture of step a) are removed by Flocculation, sedimentation or microfiltration of the microalgae culture. As a way of illustrative non limitative examples, the culture media of step a) may be centrifuged 4000 g 10 minutes.

The supernatant obtained can be alternatively lyophilized, for example during 24 hours under vacuum at 50° C. The lyophilized microalgal culture supernatant may be suspended in mQH2O obtaining a concentrated microalgal culture supernatant. In a preferred embodiment, the microalgal culture supernatant is concentrated 50-fold. Optionally, the concentrated microalgal culture supernatant may be dialyzed, as a way of illustrative non limitative example against saline buffer, for example phosphate buffered saline. Optionally, a second centrifugation may be further performed, for example a 3000 g 5 minutes or 4000 g 5 minutes in order to remove aggregates. Optionally, the microalgal culture supernatant may be filtered using for example a 0.22 um nylon filter.

In another embodiment, the supernatant of the culture of the invention is concentrated. In additional embodiments, the cell culture supernatant is concentrated at least 2-fold, 4-fold, 6-fold, 8-fold, 10-fold, 20-fold, 50-fold, 100-fold or more. In a more preferred embodiment, the cell supernatant is concentrated 50 fold. In another preferred embodiment, is 200-fold concentrated compared to initial culture volume.

In another preferred embodiment, the cells from the culture of step a) are removed and the supernatant concentrated by tangential flow filtration.

The invention also relates to a method for obtaining an IMAC-enriched microalgal culture supernatant, said method comprising the steps of
- a) culturing microalgae under conditions suitable for the growth of the microalgae and for the secretion of molecules to the culture medium,
- b) obtaining a microalgal culture supernatant by removing cells from the culture of step a),
- c) incubating the microalgal culture supernatant from step b) with a metal affinity chromatography resin under conditions allowing the binding of molecules, particularly glycoproteins, to the resin,
- d) separating the molecules, such as glycoproteins, that bind to the metal affinity chromatography resin from those that do not so bind and
- e) eluting from the resin those molecules, particularly glycoproteins, that bind to the resin, thereby obtaining an IMAC-enriched microalgal culture supernatant.

Steps c), d) and c) are performed after steps a) and b) of the method of the invention.

In a preferred embodiment, the microalgae is from Chlorophyceae class. In a more preferred embodiment, the microalgae from Chlorophyceae class are from Volvocales order. In another more preferred embodiment, the microalgae from Volvocales order are from Chlamydomonadaceae family. In another more preferred embodiment, the microalgae from Chlamydomonadaceae family is from the genus *Chlamydomonas*, more preferably is *C. reinhardtii*. All microalgae disclosed in relation to the method for obtaining a microalgal culture supernatant are equally applicable to the method for obtaining an IMAC-enriched microalgal culture supernatant.

IMAC-enriched microalgal culture supernatant as used herein relates to supernatant comprising molecules, as a way of example glycoproteins, in a more preferred embodiment having high content of histidine residues that usually are localized as tandem repeats motifs, in a histidine rich region. In a preferred embodiment the supernatant have molecules having high affinity for binding to nickel.

"High affinity" in the binding of a molecule to a metal, indicates that the complex resulting from the binding of the molecule to the metal has a dissociation constant (KD) of at least about of $10^{-7}$ M, at least about $10^{-8}$ M, at least about $10^{-9}$ M, at least about $10^{-10}$ M, or can have a Kd of at least about $10^{-11}$ M or $10^{-12}$ M or greater.

Step c) of the method of the invention for obtaining a particular culture supernatant, IMAC-enriched microalgal culture supernatant, comprises incubating the microalgal culture supernatant from step b) with a metal affinity chromatography resin under conditions allowing the binding of molecules, particularly glycoproteins, to the resin. In a particular aspect, the molecules bound to the resin are histidine-rich molecules, more particularly histidine-rich proteins, more particularly histidine-rich glycoproteins.

Before incubating the microalgal culture supernatant with the metal affinity chromatography resin, the IMAC-enriched microalgal culture supernatant obtained from step b) may be treated with a surfactant, such as Polysorbate 20 (common commercial brand names include Scattics, Alkest TW 20, Triton X-100, NP-40 and Tween 20) at a concentration 0.005%. Additionally, the IMAC-enriched microalgal culture supernatant treated with the surfactant may be centrifuged, for example at 4000 g 10 minutes, and the IMAC-enriched microalga culture supernatant may be lyophilized in order to concentrate the supernatant for example 40 folds and resuspended it in mQH2O. Optionally, the concentrated supernatant may be centrifuged, for example at 3000 g 5 minutes.

Metal affinity chromatography resin, as used herein, relates to metal ions that have been immobilized by chelation to an insoluble matrix capable of binding proteins, in this particular case nickel affinity molecules according to their affinity for said metal ions. At pH values around neutral, the amino acid histidine form complexes with the chelated metal ions (e.g., $Zn^{2+}$, $Cu^{2+}$, $Cd^{2+}$, $Hg^{2+}$, $Co^{2+}$, $Ni^{2+}$, and $Fe^{2+}$). In a preferred embodiment, the metal affinity chromatography resin is a nickel Sepharose resin. In another preferred embodiment, step c) is performed by IMAC, immobilized metal affinity chromatography.

Step d) of the method of the invention for obtaining comprises separating the molecules, such as glycoproteins, that bind to the metal affinity chromatography resin from those that do not so bind.

A person skilled in the art knows the conditions suitable for the purification of molecules. As a way of illustrative non limitative example, the resin, particularly the nickel resin, is equilibrated in appropriate buffer, for example 50 mM potassium phosphate, 50 mM potassium phosphate pH8, 0.3 M NaCl, 0.1% Triton X-100. The supernatant may be incubated with the equilibrated resin at 4° C. for 4 hours. The resin is optionally washed several times and the molecules may then be eluted by reducing the pH, increasing the mobile phase ionic strength, or adding ethylenediaminetetraacetic acid (0.05 M) to the mobile phase.

Step e) of the method for obtaining molecules, particularly glycoproteins, comprises eluting from the resin those molecules that bind to the resin, thereby obtaining a histidine-rich IMAC-enriched microalga culture supernatant. In a particular embodiment, the IMAC-enriched microalgal culture supernatant is a histidine-rich protein supernatant, more particularly is enriched or has high content of histidine-rich proteins, more particularly has high content or is enriched of histidine-rich glycoproteins.

The conditions for eluting the IMAC-enriched microalga culture supernatant from the resin are widely known by a skilled person in the art. In a particular embodiment, the elution is performed using a buffer comprising imidazole, for example a buffer containing 50 mM potassium phosphate, 0.3 M NaCl, 0.1% Triton X-100, 0.5M imidazole. The eluted IMAC-enriched microalgal culture supernatant may be further concentrated and diafiltrated, for example in 50 mM potassium phosphate pH8, 50 mM NaCl. Alternatively, BSA may be further added at a final concentration of 0.1% (w/v).

Once the IMAC-enriched microalgal culture supernatant is eluted from the IMAC column, it can be concentrated using any means known in the art. In another embodiment, the histidine-rich protein composition is concentrated at least 2-fold, 4-fold. 6-fold, 8-fold, 10-fold, 20-fold, 50-fold, 100-fold or more. In a more preferred embodiment, the supernatant is concentrated 53-fold.

The histidine-rich molecules protein composition resulting from the method of the invention comprises histidine-rich molecules, more particularly histidine-rich proteins, more particularly histidine-rich glycoproteins, that are enriched at least 2-fold, at least 4-fold, at least 8-fold, at least 10-fold, at least 20-fold, at least 30-fold, at least 40-fold, at least 50-fold, at least 60-fold, at least 70-fold, at least 80-fold, at least 90-fold, at least 100-fold, at least 200-fold, at least 300-fold, at least 400-fold, at least 500-fold, at least 600-fold, at least 700-fold, at least 800-fold, at least 900- fold, at least 1000-fold, at least 10000-fold, at least 100.000-fold, at least $10^6$-fold, at least $10^7$-fold, at least $10^8$-fold or more with respect to the starting material comprising the cell-free culture.

In a more preferred embodiment, the IMAC-enriched microalgal culture supernatant obtained by a method of the invention comprises glycoproteins, more particularly histidine-rich glycoproteins.

Microalgal Culture Supernatant, Combinations and Cell Culture Media

In another aspect, the invention relates to a microalgal culture supernatant obtained by a method according to the invention.

The microalgal culture supernatant and the IMAC-enriched microalgal culture supernatant are the microalgal culture supernatants obtained by a method of the invention, and thus they are micro algal culture supernatants of the invention.

It will be understood that the culture supernatant obtained according to the first method of the invention does not necessarily need to consist exclusively on glycoproteins but that it may contain also other components such as non-glycosylated proteins (i.e. proteins that are secreted but which do not contain any glycosyl residues), as well as other products which are secreted by microalgae when cultured including but not limited to phycocyanin/allophycocyanin, *Chlorella* growth factor (CGF), chlorophyll carotenoids (astaxanthin, fucoxanthin, lutein and the like), fatty acids (EPA, DHA) as glycero lipids, phycoerythrin, exopolysaccharides, organic acids such as L-ascorbic acid, lactic acid, 5-amino levulinic acid and glycolic acid, phytohormones such as abcisic acid, indole-3-acetic acid, gibberellic acid, carbohydrates, nucleic acids, peptides and the like In a preferred embodiment, the microalgal culture supernatant and the IMAC-enriched microalgal culture supernatant obtained by a method of the invention comprises glycoproteins.

In some embodiments, the content of glycoproteins in the supernatant with respect to the total amount of protein is of at least 50% (w/w), at least 60% (w/w), at least 70% (w/w), at least 80% (w/w), at least 90% (w/w), w), at least 91% (w/w), at least 92% (w/w), at least 93% (w/w), at least 94% (w/w), at least 95% (w/w), at least 96% (w/w), at least 97% (w/w), at least 98% (w/w), at least 99% (w/w), at least 99.5% (w/w), w), at least 99.9% (w/w), at least 99.99% (w/w) or more.

In a preferred embodiment, the microalgal culture supernatant is an IMAC-enriched microalgal culture supernatant.

In some embodiments, the content of histidine-rich molecules, more particularly histidine-rich proteins, more particularly histidine-rich glycoproteins in the composition with respect to the total amount of glycoproteins is of at least 50% (w/w), at least 60% (w/w), at least 70% (w/w), at least 80% (w/w), at least 90% (w/w), w), at least 91% (w/w), at least 92% (w/w), at least 93% (w/w), at least 94% (w/w), at least 95% (w/w), at least 96% (w/w), at least 97% (w/w), at least 98% (w/w), at least 99% (w/w), at least 99.5% (w/w), w), at least 99.9% (w/w), at least 99.99% (w/w) or more. In a more preferred embodiment the histidine-rich molecules are histidine-rich proteins, more particularly histidine-rich glycoproteins.

In another preferred embodiment, the microalgal culture supernatant comprises more than 1 µg/L of protein, particularly between 1 µg/L and 0.1 g/L of protein, more particularly 1 µg/L and 50 mg/1, more particularly between 1 µg/L and 10 mg/L, more particularly between 1 µg/L and 5 mg/L, more particularly between 1 µg/L and 1 mg/L, more particularly between 1 µg/L and 500 µg/L, more particularly between 1 µg/L and 100 µg/L. In another particular embodiment, the microalgal culture supernatant comprises between 100 and 400 µg/L of protein. Any method suitable for determining the amount of proteins may be used in the present invention, for example any spectrophotometric assay such as Bradford, BCA method and the Lowry method.

In another preferred embodiment, the microalgal culture supernatant obtained by a method of the invention comprises proteins having 1-500 kDa, more preferably 10 to 400 kDa, more preferably 20 to 350 kDa, more preferable 30 to 300 kDa, more preferably 40 to 250 kDa, more preferably 50 to 200 kDa, more preferably 60 to 150 kDa, more preferably 70 to 125 kDa.

In another preferred embodiment, the microalgal culture supernatant obtained by a method of the invention comprises between 0.001 mg/L and 10 g/L of carbohydrates. In a particular embodiment, particularly between 0.001 mg/L and 1 mg/L, more particularly between 0.001 mg/L and 10 mg/L, more particularly between 0.001 mg/L and 100 mg/L, more particularly between 0.001 mg/L and 1 g/L, more particularly between 0.001 mg/L and 10 g/L. In another preferred embodiment, microalgal culture supernatant obtained by a method of the invention comprises between 2-6 g/l of carbohydrates.

The inventors have observed that the microalgal culture supernatant of the invention acts synergistically with a growth factor. Therefore, in another aspect, the invention relates to a combination comprising a microalgal culture supernatant obtained by a method of the invention and a growth factor.

"Combination", as used herein, is meant either, simultaneous administration or any manner of separate or sequential administration of (i) a microalgal culture supernatant obtained by a method of the invention and (ii) a growth factor. The term "combination" also stands for the various combinations of compounds (i) and (ii), for example in a single composition, in a combined mixture composed from separate formulations of the single active compounds, such as a "tank-mix", and in a combined use of the single active ingredients when applied in a sequential manner, i.e. one after the other with a reasonably short period, such as a few hours or days or in simultaneous administration.

Preferably, if the administration is not simultaneous, the compounds are administered in a close time proximity to each other. Furthermore, it does not matter if the compounds are administered in the same dosage form or by the same route, e.g. one compound may be administered topically and the other compound may be administered orally. Suitably, both compounds are administered orally or topically.

Therefore, a combination of at least one of (i) a microalgal culture supernatant obtained by a method of the invention and (ii) a growth factor may be formulated for its simultaneous, separate or sequential administration. This has the implication that the combination of the two compounds may be administered:
  as a combination that is being part of the same formulation, the two compounds being then administered always simultaneously.
  as a combination of two units, each with one of the substances giving rise to the possibility of simultaneous, sequential or separate administration.

"Growth factor", as used herein relates to a molecule capable of stimulating cellular growth, proliferation, healing, and or cellular differentiation. Illustrative, non-limitative examples of growth factor that may be used in the present invention are Epidermal growth factor (EGF), Fibroblast growth factor (FGF), keratinocyte growth factor (KGF), Platelet derived growth factor (PDGF), Insulin-like growth factor (IGF) In a more preferred embodiment, the growth factor is EGF, more preferably EGF from human. EGF relates to a 6 kDa protein that stimulates cell growth and differentiation that in human corresponds to the sequence with accession number Q6QBS2 in the Uniprot database 28 Feb. 2018.

In another aspect, the invention relates to a cell culture media comprising a microalgal culture supernatant of the invention or a combination of the invention.

Cell culture media as used herein relates to a solid, liquid or semi-solid designed to support the growth of microorganisms or cells or plants. Culture media contain all the elements that most cells need for growth such as a carbon source, water, various salts and a source of amino acids and nitrogen.

In a preferred embodiment, the cell culture media of the invention is suitable for culturing mammal cells, more particularly cells from connective tissue, more particularly fibroblasts.

The inventors have observed that the microalgal culture supernatant of the invention acts synergistically with the action of a growth factor. Therefore, in a particular aspect of the cell culture media, the content of serum in the media is reduced, preferably is lower than 10%, more preferably 8%, 7%, 6%, 5%, 4%, 3%, 2%, 1% or more preferably 0.5% (v/v).

All the terms and embodiments previously described are equally applicable to this aspect of the invention.

Cosmetic Composition and Uses Thereof

In another aspect, the invention relates to a cosmetic composition or cosmeceutical comprising a cosmetically acceptable adjuvant and
  (i) a microalgal culture supernatant obtained by a method comprising the steps of:
    a) culturing microalgae belonging to Chlorophyceae class or Volvocales order under conditions suitable for the growth of the microalgae and for the secretion of molecules to the culture medium, and
    b) obtaining a microalgal culture supernatant by removing cells from the culture of step a),
  (ii) an IMAC-enriched microalgal culture supernatant obtained by a method comprising the steps of
    a) culturing microalgae under conditions suitable for the growth of the microalga and for the secretion of molecules to the culture medium,
    b) obtaining a microalgal culture supernatant by removing cells from the culture of step a),
    c) incubating the microalgal culture supernatant from step b) with a metal affinity chromatography resin under conditions allowing the binding of molecules to the resin of those molecules in the supernatant which show affinity to the resin,
    d) separating the molecules that bind to the metal affinity chromatography resin from those that do not so bind and
    e) eluting from the resin those molecules that bind to the resin, thereby obtaining an IMAC-enriched microalgal culture supernatant, or
  (iii) a combination comprising a growth factor, and a microalgal culture supernatant as defined in (i) or an IMAC-enriched microalgal culture supernatant as defined in (ii).

In a preferred embodiment, the microalgae is from Chlorophyceae class. In a more preferred embodiment, the microalgae from Chlorophyceae class are from Volvocales order. In another more preferred embodiment, the microalgae from Volvocales order are from Chlamydomonadaceae family. In another more preferred embodiment, the microalgae from Chlamydomonadaceae family is from the genus *Chlamydomonas*, more preferably is *C. reinhardtii*. All microalgae disclosed in relation to the methods for obtaining a microalgal culture supernatant are equally applicable to this aspect of the invention.

In another preferred embodiment, the cosmetic composition of the invention comprises glycoproteins, more particularly histidine-rich glycoproteins.

The term "cosmetic composition" or "personal care composition", as used herein, refers to a composition suitable for use in personal hygiene of human beings or animals, or in order to enhance the natural beauty or change the body appearance without affecting the structure or functions of the human or animal body, comprising one or more products providing such effects. If desired, the cosmetic composition provided by the invention can contain, in addition to the active product of the invention, one or more cosmetics or cosmetic products, i.e., substances or mixtures intended to be placed in contact with the external parts of the human or animal body (e.g., epidermis, hair system, nails, lips, etc.) or with the teeth and the buccal mucosa, for the exclusive or main purpose of cleaning them, perfuming them, changing their appearance, protecting them, keeping them in good condition or correcting body odors. Illustrative examples of cosmetically acceptable vehicles include the products contained in the INCI (International Nomenclature of Cosmetic Ingredients) list. Cosmetic or personal care compositions include products such as balms, pads, pomades, creams, etc. oils, surfactants, humectants, botanical extracts, vitamins, antioxidants, sunscreen agents, perfumes, preservatives, and the like.

The percentage (w/w) of glycoproteins or of the histidine-rich glycoproteins composition in the cosmetic composition for use in the cosmetic method according to the invention is from 0.00001 and 50 percent in weight, preferably between 0.0001 and 40 percent in weight, and more preferably between 0.001 and 30 percent in weight, preferably between 0.1 to 20 percent by weight, more preferably from 0.2 to 10 percent by weight and better still from 0.5 to 2 percent by weight, with respect to the total weight of the composition.

"Cosmeceutical", as used herein refers to a product suitable for use in the body or animal body comprising one or more cosmeceutical products (functional cosmetics, dermaceuticals or active cosmetics), i.e., topical hybrid products with cosmetic-pharmaceutical characteristics containing active ingredients having effect on user's skin, hair and/or nails, at higher and more effective concentrations, therefore they are located in an intermediate level between cosmetic and drug. Illustrative examples of cosmeceutical products include essential oils, ceramides, enzymes, minerals, peptides, vitamins, etc.

"Cosmetically acceptable excipient" or a cosmetically active ingredient is a compound or mixture of compounds that exerts a beneficial effect on the skin such as improving or maintaining the cosmetic qualities of the skin, for example the level of hydration, elasticity, firmness, gloss, tone and texture, among others.

In a particular embodiment, the cosmetically acceptable ingredient is selected from the group consisting of antioxidants, moisturizers, skin conditioning agents, antistatic agents, smoothing agents, soothing agents, emollient agents, astringent agents, antiseborrheic agents, antidandruff agents, tonics, bleaching agents, cleansing agents, keratolytic agents, refatting agents, lifting agents, anti-wrinkle agents, repairing agents, regenerating agents, firming agents, energizing agents, volumizing agents, anti-dark circle agents, anti-puffiness agents, pore minimizing agents, protective agents and mixtures thereof; or antimicrobial agents, anti-inflammatory agents and fungicides.

An antioxidant is a compound which inhibits reactions promoted by oxygen, thus avoiding oxidation reactions. These compounds also avoid rancidity of the compositions. Non-limiting examples of antioxidants are *Camellia sinensis* leaf extract, trans-resveratrol, alpha lipoic acid, nordihydroguaiaretic acid, caffeine, Aloe vera, ascorbyl palmitate, alpha-arbutin, arbutin, *Echinacea purpurea* extract, niacinamide and astaxanthine.

A moisturizer is a compound that increases the water content of the skin and helps to keep it soft and smooth. Non-limiting examples of moisturizers are *Echinacea purpurea* extract, niacinamide and pyroglutamic acid.

A skin conditioning agent is a compound that maintains the skin in good condition. Non-limiting examples of skin conditioning agents are *Echinacea purpurea* extract, *Camellia sinensis* leaf extract, salicylic acid, biotin, *Helichrysum arenarium* flower extract, *Chamomilla recutita* flower extract, *Ginkgo biloba* leaf extract, Aloe vera, caprylyl glycol, *Ranunculus ficaria* extract, *Centella asiatica* extract, *Aesculus hippocastanum* seed extract, ethyl nicotinate, glycyrrhetinic acid, alpha-arbutin, arbutin, *Enantia chlorantha* bark extract, astaxanthin, *Spilanthes acmella* flower extract and benzyl nicotinate.

An antistatic agent is a compound that reduces static electricity by neutralizing electrical charge on a surface. Non-limiting examples of antistatic agents are niacin, acrylate copolymer and benzyl nicotinate.

A smoothing agent is a compound that decreases skin roughness or irregularities, thus achieving an even skin surface. Non-limiting examples of smoothing agents are niacin, *Spirulina maxima* extract, niacinamide and *Centella asiatica* extract.

A soothing agent is a compound that helps alleviate discomfort of the skin or of the scalp. Non-limiting examples of soothing agents are methyl nicotinate, *Centella asiatica* extract and *Echinacea purpurea* extract.

An emollient agent is a compound that softens the skin. Non-limiting examples of emollient agents are *Camellia sinensis* leaf extract, *Panax ginseng* root extract, glyceryl stearate and caprylyl glycol.

An astringent agent is a compound that contracts the skin. A non-limiting example of an astringent agent is *Camellia sinensis* leaf extract.

An antiseborrheic agent is a compound that helps control sebum production. Non-limiting examples of antiseborrheic agents are biotin and *Enantia chlorantha* bark extract.

An antidandruff agent is a compound that helps control dandruff. A non-limiting example of an antidandruff agent is salicylic acid.

A tonic is a compound that produces a feeling of well-being on skin and hair. Non-limiting examples of tonics are *Echinacea purpurea* extract, *Camellia sinensis* leaf extract, *Panax ginseng* root extract, methyl nicotinate and *Centella asiatica* extract.

A bleaching agent is a compound that lightens skin tone or corrects imperfections in the skin's pigmentation by lessening the concentration of melanin. Non-limiting examples of bleaching agents are glabridin, alpha-arbutin and arbutin.

A cleansing agent is a compound that helps to keep the body surface (skin and/or hair) clean. Non-limiting examples of cleansing agents are *Centella asiatica* extract and alpha lipoic acid.

A keratolytic agent is a compound that helps to eliminate the dead cells of the stratum corneum. A non-limiting example of a keratolytic agent is salicylic acid.

A refatting agent is a compound that replenishes the lipids of the hair or of the top layers of the skin. A non-limiting example of a refatting agent is C(6)-ceramide.

A lifting agent is a compound that that lifts the skin. A non-limiting example of a lifting agent is acrylate copolymer.

An anti-wrinkle agent is a compound that can reduce fine lines on the skin. Non-limiting examples of anti-wrinkle agents are ascorbyl palmitate and niacinamide.

A repairing agent is a compound that helps the body to restore skin alterations, such as scars. Non-limiting examples of repairing agents are *Centella asiatica* extract and *Echinacea purpurea* extract.

A regenerating agent is a compound that helps in skin self-generation by means of mechanisms such as cell stimulation. A non-limiting example of a regenerating agent is *Centella asiatica* extract.

A firming agent is a compound that provides firmness to the skin. Non-limiting examples of firming agents having suitable $\delta D$, $\delta P$ and $\delta H$ values are biotin and niacinamide.

An energizing agent is a compound that provides in a combined manner brightness and astringency to the skin. Non-limiting examples of energizing agents are trans-resveratrol, *Panax ginseng* root extract, *Camellia sinensis* leaf extract.

A volumizing agent is a compound that stimulates skin adipocytes. A non-limiting example of a volumizing agent is *Centella asiatica* extract.

An anti-dark circle agent is a compound that reduces pigmented areas under the eyes. Non-limiting examples of anti-dark circle agents are caffeine, *Camellia sinensis* leaf extract and Gingko *biloba* leaf extract.

An anti-puffiness agent is a compound that reduces swelling, generally in the area around the eye. Non-limiting examples of anti-puffiness agents are caffeine, *Aesculus hippocastanum* seed extract and *Chamomilla recutita* flower extract.

A pore minimizing agent is a compound that helps to clean out pores and make them look smaller. A non-limiting example of a pore minimizing agent is *Ranunculus ficaria* extract.

A protective agent is a compound that protects the skin against external agents. Non-limiting examples of protective agents are trans-resveratrol, *Centella asiatica* extract and niacinamide.

An antimicrobial agent is a compound that helps to control the growth of microorganisms on the skin. Non-limiting examples of antimicrobial agents are *Camellia sinensis* leaf extract, ferulic acid, hexyl resorcinol, *Enantia chlorantha* bark extract and *Spilanthes camella* flower extract.

A fungicide is a compound that helps to control the growth of fungi on the skin. A non-limiting example of a fungicide values is pyraclostrobin.

An anti-inflammatory agent is a compound that reduces inflammation. A non-limiting example of an anti-inflammatory agent is glabridin.

The invention also relates to a cosmetic method for skin care which comprises administration to a subject of a cosmetic composition or cosmeceutical comprising a cosmetically acceptable adjuvant and
  (i) a microalgal culture supernatant obtained by a method comprising the steps of:
    a) culturing microalgae belonging to Chlorophyceae class or Volvocales order under conditions suitable for the growth of the microalgae and for the secretion of molecules to the culture medium, and
    b) obtaining a microalgal culture supernatant by removing cells from the culture of step a),
  (ii) an IMAC-enriched microalgal culture supernatant obtained by a method comprising the steps of
    a) culturing microalgae under conditions suitable for the growth of the microalgae and for the secretion of molecules to the culture medium,
    b) obtaining a microalgal culture supernatant by removing cells from the culture of step a),
    c) incubating the microalgal culture supernatant from step b) with a metal affinity chromatography resin under conditions allowing the binding of those molecules in the supernatant showing affinity to the resin,
    d) separating the molecules that bind to the metal affinity chromatography resin from those that do not so bind and
    e) eluting from the resin those molecules that bind to the resin, thereby obtaining an IMAC-enriched microalga culture supernatant, or a
  (iii) a combination comprising a growth factor, and a microalgal culture supernatant as defined in (i) or an IMAC-enriched microalgal culture supernatant as defined in (ii).

In addition, the invention relates to a cosmetic method for a condition which requires increased proliferation of fibroblasts which comprises administration to a subject of a cosmetic composition or cosmeceutical comprising a cosmetically acceptable adjuvant and
  (i) a microalgal culture supernatant obtained by a method comprising the steps of:
    a) culturing microalgae belonging to Chlorophyceae class or Volvocales order under conditions suitable for the growth of the microalgae and for the secretion of molecules to the culture medium, and
    b) obtaining a microalgal culture supernatant by removing cells from the culture of step a),
  (ii) an IMAC-enriched microalgal culture supernatant obtained by a method comprising the steps of
    a) culturing microalgae under conditions suitable for the growth of the microalgae and for the secretion of molecules to the culture medium,
    b) obtaining a microalgal culture supernatant by removing cells from the culture of step a),
    c) incubating the microalgal culture supernatant from step b) with a metal affinity chromatography resin under conditions allowing the binding of those molecules in the supernatant showing affinity to the resin,
    d) separating the molecules that bind to the metal affinity chromatography resin from those that do not so bind and
    e) eluting from the resin those molecules that bind to the resin, thereby obtaining an IMAC-enriched microalga culture supernatant, or a
  (iii) a combination comprising a growth factor, and a microalgal culture supernatant as defined in (i) or an IMAC-enriched microalgal culture supernatant as defined in (ii), and wherein the method is performed in the presence of reduced amounts of fetal serum or growth factors.

"Reduced amount of fetal serum or growth factors", as used herein relates to a content of serum or growth factors in the media or in the cosmetic composition or cosmeceutical preferably lower than 10%, more preferably 8%, 7%, 6%, 5%, 4%, 3%, 2%, 1% or more preferably 0.5% (v/v).

"Growth factors" as used herein relates to substances capable of stimulating cellular growth.

"Fetal serum" as used herein relates to a supplement for cell culture media obtained from the blood of a fetus for example bovine fetus.

The cosmetic composition of the invention also relates to the cosmetic treatment of mucous membranes, hair and/or nails.

"Skin care", as used herein relates to the care of sensitive, irritable skin, having tendency to pimple, itching and redness, lichenification, xeriss, redness, blistering, oozing, crusting, scaling, thickening and color change. In a particular aspect, the cosmetic composition of the invention is for anti-wrinkle treatment of the skin. "A condition which requires increased proliferation of fibroblasts" relates to any condition which requires increased number or proliferation of fibroblasts. In a preferred embodiment, the cosmetic condition which requires increased proliferation of fibroblast is selected from the group consisting of premature skin aging, chronological aging, photoaging and cutaneous senescence.

The cosmetic composition can be administered at any route, for example, by systemic (e.g. intravenous, subcutaneous, intramuscular injection), oral, parenteral or topical administration. Additionally, it is also possible to administer the cosmetic compositions of the invention as defined above intranasally or sublingually which allows systemic administration by a non-aggressive mode of administration. In a particular embodiment, the cosmetic composition is topically administered. In another particular embodiment is intradermically administered.

In a preferred embodiment, the microalgae is from Chlorophyceae class. In a more preferred embodiment, the microalgae from Chlorophyceae class are from Volvocales order. In another more preferred embodiment, the microalgae from Volvocales order are from Chlamydomonadaceae family. In another more preferred embodiment, the microalgae from Chlamydomonadaceae family is from the genus *Chlamydomonas*, more preferably is *C. reinhardtii*. All microalgae disclosed in relation to the methods for obtaining a microalgal culture supernatant are equally applicable to this aspect of the invention.

The cosmetic composition of the invention is administered in a cosmetic effective amount.

The term "cosmetic effective amount", as used herein, relates to the sufficient amount of a compound (i.e. of the composition of the invention) to provide the desired effect and it will generally be determined, by among other causes, the characteristics of the compound itself and the cosmetic effect to be achieved. The dosage for obtaining a cosmetic effective amount it will also depend on a range of factors, such as, for example, age, weight, sex or tolerance of the animal, preferably a mammal and more preferably human.

The stimulatory activity on the proliferation and structural organization of fibroblasts promoted by the microalgal culture supernatant preparation and the IMAC-enriched microalgal culture supernatant preparation according to the invention may be used to increase the renewal and regeneration capabilities of the skin and thereby to provide a rejuvenation effect. Therefore, in a particular embodiment of the invention, the compositions of the invention are used for the prevention and treatment of chronological aging.

In another embodiment, the cosmetic compositions according to the invention are used for the treatment or prevention of photoaging. In a similar fashion to the above mentioned effect on the prevention and treatment of chronological aging, photoaging of the skin may be partially reversed by topical treatment with the cosmetic compositions according to the invention due to the promotion of the proliferation and structural organization of fibroblasts.

In another embodiment, the cosmetic methods of the invention are useful for the treatment or as aid in the treatment or prevention of skin pigmentation disorders (i.e. melasma). The topical treatment of the skin with the methods according to the invention prevents the excessive thickening of the stratum corneum, *granulosum* and *spinosum*. These results in a reduction of the amount of any kind of pigment accumulation that may be entrapped into the outermost layers of the skin and therefore treatment with the cosmetic compositions according to the invention may induce an efficient reduction of the intensity and even number of pigment spots.

In additional embodiments, the compositions according to the invention are useful for improving the condition and aesthetic appearance of skin affected by aging, particularly matured or maturing skin, by anyone of the following methods: reducing dermatological signs of chronological aging, photo-aging, hormonal aging, and/or actinic aging; preventing and/or reducing the appearance of lines and/or wrinkles; reducing the noticeability of facial lines and wrinkles, facial wrinkles on the cheeks, forehead, perpendicular wrinkles between the eyes, horizontal wrinkles above the eyes, and around the mouth, marionette lines, and particularly deep wrinkles or creases; preventing, reducing, and/or diminishing the appearance and/or depth of lines and/or wrinkles; improving the appearance of suborbital lines and/or periorbital lines; reducing the appearance of crow's feet; rejuvenating and/or revitalizing skin, particularly aging skin; reducing skin fragility; ameliorating the effects of estrogen imbalance; preventing and/or treating skin atrophy; preventing, reducing, and/or treating hyperpigmentation; minimizing skin discoloration; improving skin tone, radiance, clarity and/or tautness; preventing, reducing, and/or ameliorating skin sagging; improving skin firmness, plumpness, suppleness and/or softness; improving procollagen and/or collagen production; improving skin texture and/or promoting retexturization; improving skin barrier repair and/or function; improving the appearance of skin contours; restoring skin luster and/or brightness; minimizing dermatological signs of fatigue and/or stress; resisting environmental stress; replenishing ingredients in the skin decreased by aging and/or menopause; improving communication among skin cells; increasing cell proliferation and/or multiplication; increasing skin cell metabolism decreased by aging and/or menopause; retarding cellular aging; improving skin moisturization; enhancing skin thickness; increasing skin elasticity and/or resiliency; enhancing exfoliation; improving microcirculation; decreasing and/or preventing cellulite formation; thickening skin tissue (i.e., building the epidermis and/or dermis layers of the skin and where applicable the keratinous layers of the nail and hair shaft), preventing and/or retarding atrophy of mammalian skin, preventing and/or retarding the appearance of spider vessels and/or red blotchiness on mammalian skin, preventing and/or retarding the appearance of dark circles under the eye of a mammal, preventing and/or retarding sallow-colored mammalian skin, preventing and/or retarding sagging of mammalian skin, softening and/or smoothing lips, hair and nails of a mammal, preventing and/or relieving itch of mammalian skin, regulating skin texture (e.g. wrinkles and fine lines), and improving skin color (e.g. redness, freckles) and any combinations thereof.

All the terms and embodiments previously described are equally applicable to this aspect of the invention.

Pharmaceutical Composition as Uses Thereof

In another aspect, the invention relates to a pharmaceutical composition comprising a pharmaceutically acceptable adjuvant and
- (i) a microalgal culture supernatant obtained by a method comprising the steps of:
  - a) culturing microalgae belonging to Chlorophyceae class or Volvocales order under conditions suitable for the growth of the microalgae and for the secretion of molecules to the culture medium, and
  - b) obtaining a microalgal culture supernatant by removing cells from the culture of step a),
- (ii) an IMAC-enriched microalgal culture supernatant obtained by a method comprising the steps of
  - a) culturing microalgae under conditions suitable for the growth of the microalgae and for the secretion of molecules to the culture medium,
  - b) obtaining a microalgal culture supernatant by removing cells from the culture of step a),
  - c) incubating the microalgal culture supernatant from step b) with a metal affinity chromatography resin under conditions allowing the binding of molecules to the resin of those molecules in the supernatant which bind to the resin,
  - d) separating the molecules that bind to the metal affinity chromatography resin from those that do not so bind and
  - e) eluting from the resin those molecules that bind to the resin, thereby obtaining an IMAC-enriched microalga culture supernatant or
- (iii) a combination comprising a growth factor, and a microalgal culture supernatant as defined in (i) or an IMAC-enriched microalgal culture supernatant as defined in (ii).

"Pharmaceutical composition", as used herein, relates to compositions and molecular entities that are physiologically tolerable. Preferably, the term "pharmaceutically acceptable" means it is approved by a regulatory agency of a state or federal government or is included in the U.S. Pharmacopoeia or other generally recognized pharmacopoeia for use in animals, and more particularly in humans.

In a preferred embodiment, the microalgae is from Chlorophyceae class. In a more preferred embodiment, the microalgae from Chlorophyceae class are from Volvocales order. In another more preferred embodiment, the microalgae from Volvocales order are from Chlamydomonadaceae family. In another more preferred embodiment, the microalgae from Chlamydomonadaceae family is from the genus *Chlamydomonas*, more preferably is *C. reinhardtii*. All microalgae disclosed in relation to the methods for obtaining a microalga culture supernatant are equally applicable to this aspect of the invention.

In another preferred embodiment, the pharmaceutical composition of the invention comprises glycoproteins, more particularly histidine-rich glycoproteins.

Appropriate amounts of a compound of the combination of the invention as defined above can be formulated with pharmaceutically acceptable excipients and/or carriers to obtain a pharmaceutical composition for use in medicine, particularly for use in wound healing or for repairing skin damage.

The percentage (w/w) of glycoproteins or of the histidine-rich glycoproteins composition in the pharmaceutical composition according to the invention is from 0.00001 and 50 percent in weight, preferably between 0.0001 and 40 percent in weight, and more preferably between 0.001 and 30 percent in weight, preferably between 0.1 to 20 percent by weight, more preferably from 0.2 to 10 percent by weight and better still from 0.5 to 2 percent by weight, with respect to the total weight of the composition.

The term "excipient" refers to a vehicle, diluent or adjuvant that is administered with the active ingredient. Such pharmaceutical excipients can be sterile liquids, such as water and oils, including those of petroleum, animal, vegetable or synthetic origin, such as peanut oil, soybean oil, mineral oil, sesame oil and similar. Water or saline aqueous solutions and aqueous dextrose and glycerol solutions, particularly for injectable solutions, are preferably used as vehicles. Suitable pharmaceutical vehicles are described in "Remington's Pharmaceutical Sciences" by E. W. Martin, 21st Edition, 2005; or "Handbook of Pharmaceutical Excipients", Rowe C. R.; Paul J. S.; Marian E. Q., sixth Edition. Suitable pharmaceutically acceptable vehicles include, for example, water, salt solutions, alcohol, vegetable oils, polyethylene glycols, gelatin, lactose, amylose, magnesium stearate, talc, surfactants, silicic acid, viscous paraffin, perfume oil, monoglycerides and diglycerides of fatty acids, fatty acid esters petroetrals, hydroxymethyl cellulose, polyvinylpyrrolidone and similars.

The pharmaceutical compositions containing the combination of the invention as defined above can occur at any pharmaceutical form of administration considered appropriate for the selected administration route, for example, by systemic (e.g intravenous, subcutaneous, intramuscular injection), oral, parenteral or topical administration, for which it will include the pharmaceutically acceptable excipients necessary for formulation of the desired method of administration. Additionally, it is also possible to administer the composition of the invention as defined above intranasally or sublingually which allows systemic administration by a non-aggressive mode of administration. A particular route of delivery is topical. Another particular route is intradermal.

Those skilled in the art are familiar with the principles and procedures discussed.

In another aspect the invention relates to a pharmaceutical composition comprising the microalgal culture supernatant according to the invention or the combination according to the invention and a pharmaceutically acceptable adjuvant for use in medicine.

The invention relates to a pharmaceutical composition of the invention or a combination of the invention for use in wound healing or repair of skin damage.

Alternatively, the invention relates to the use of a pharmaceutical composition or combination of the invention for the preparation of a medicament for using in wound healing or for repairing skin damage.

Alternatively, the invention relates to a method for treating wound healing or repairing skin damage which comprises administering a pharmaceutical composition or a combination of the invention to a subject in need thereof.

Wound healing as used herein relate to is an intricate process in which the skin repairs itself after injury. Healing is the interaction of a complex cascade of cellular events that generates resurfacing, reconstitution, and restoration of the tensile strength of injured skin. Healing is a systematic process, traditionally explained in terms of 4 overlapping steps. Particularly, the pharmaceutical composition or combination of the invention is useful in the proliferation and maturation steps of wound healing.

The term "wound" used in the present context means any wound (see below for a classification of wounds) and in any particular phase of the healing process, including the phase before having started any healing or even before a specific wound is produced, such as a surgical incision (prophylactic treatment). Wounds are typically classified in one of four stages depending on the depth of the wound. Thus, stage I wounds are those limited to the epithelium, stage II wounds are those extending to the dermis, stage III wounds are those extending to the subcutaneous tissue and stage IV wounds are those in which the bone is exposed.

Examples of wounds which can be prevented and/or treated according to the present invention are, for example, open wounds and closed wounds. Open wounds which can be treated with the compositions of the invention include, but are not limited to, burns caused cold or heat, incisions, ulcers, lacerations, abrasions, acne, bite wounds, punctures or gunshot wounds or closed wounds such as contusions or hematomas, lesions of the blood and lymphatic vessels such as Buerger's disease, lymphedema and ulcus cruris, post-surgery wounds such as wounds after a skin transplant and sutured wounds, decubitus ulcer, pressure ulcer, diabetic ulcer, post-herpetic ulcers and lesions by irradiation. Closed wounds which can be treated with the compositions of the invention include, but are not limited to, contusions or hematomas.

Aseptic wounds, contused wounds, incised wounds, lacerated wounds, non-penetrating wounds (i.e., wounds in which there is no discontinuity of the skin, but there is lesion in the underlying structures), open wounds, penetrating wounds, perforating wounds, punctured wounds, septic wounds, subcutaneous wounds, etc can also be treated according to the present invention. Examples of sores are decubitus ulcers, aphthae, chrome ulcers, cold ulcers, pressure ulcers, etc. Examples of ulcers are, for example, peptic ulcer, duodenal ulcer, gastric ulcer, gouty ulcer, diabetic ulcer, hypertensive ischemic ulcer, stasis ulcer, ulcus cruris (venous ulcer), sublingual ulcer, submucosal ulcer, symptomatic ulcer, trophic ulcer, tropical ulcer and venereal ulcer, for example caused by gonorrhea (including urethritis, endocervicitis and proctitis). The conditions related to wounds or sores which can be successfully treated according to the invention are burns, anthrax, tetanus, gaseous gangrene, scarlatina, erysipelas, sycosis barbae, folliculitis, impetigo contagiosa or bullous impetigo, etc. There is frequently an overlapping between the use of the terms "wound" and "ulcer" and "wound" and "sore" and, moreover, the terms are often used randomly. Therefore, as has been previously mentioned, in the present context the term "wound" includes the terms "ulcer", "lesion", "sore" and "infarction" and the terms are used indistinctly unless otherwise indicated.

The types of wounds to be treated according to the invention also include i) general wounds, such as, for example, surgical, traumatic, infectious, ischemic, thermal, chemical and bullous wounds; ii) specific wounds of the oral cavity, such as, for example, wounds after extractions, endodontic wounds especially in relation to the treatment of cysts and abscesses, ulcers and bacterial, viral or autoimmune lesions, mechanical, chemical, thermal, infectious and lichenoid wounds; herpetic ulcers, aphthous stomatitis, acute necrotizing ulcerative gingivitis and burning mouth syndrome are specific examples; and iii) wounds on the skin, such as, for example, neoplasias, burns (for example, chemical or thermal burns), lesions (bacterial, viral, autoimmune), bite wounds and surgical incisions. Another way to classify the wounds is as i) small loss of tissue due to surgical incisions, minor abrasions and minor bite wounds, or as ii) significant loss of tissue. This latter group includes ischemic ulcers, pressure sores, fistulas, lacerations, severe bite wounds, thermal burns and wounds in donor site (in soft and hard tissues) and infarctions.

Another type of wounds that can be treated according to the invention include diabetic foot wounds, caused by the disease of the arteries that irrigate the foot and often complicated by periferic nerve damage and infection, that can produce injuries, ulcers and atrophy of skin and gangrene.

Another further type of wounds treatable by the invention are varicose ulcer wounds, that are a type of venous ulcer characterized by the loss of continuity of the skin on a region with varicose conditions that can appear after a simple trauma.

In a preferred embodiment the composition of the invention is used for the treatment of a wound in which the wound is selected from the group consisting of an aseptic wound, a contused wound, an incised wound, a lacerated wound, a non-penetrating wound, an open wound, a penetrating wound, a perforating wound, a punctured wound, a septic wound, a subcutaneous wound, an ischemic ulcer, a pressure ulcer, a fistula, a bite wound, a thermal burn wound, a diabetic foot wound and a donor site wound.

In another preferred embodiment, the microalgal culture supernatant or the pharmaceutical composition of the invention are used for the healing of a wound wherein the wound is selected from the group consisting of an aseptic wound, a contused wound, an incised wound, a lacerated wound, a non-penetrating wound, an open wound, a penetrating wound, a perforating wound, a punctured wound, a septic wound, a subcutaneous wound, an ischemic ulcer, a pressure sore, a fistula, a bite wound, a thermal burn, a donor site wound, a diabetic foot wound and a varicose ulcer wound.

As used in the present invention "healing" of a wound refers to the physiological process in which the wounded (damaged) area returns to its normal state. If it refers to an open wound, the healing refers to the process by which the skin or mucosa again forms a continuous barrier by means of the increase of connective tissue and of epithelial cells. The person skilled in the art will appreciate that, after the healing, the wounded area can comprise scar tissue which is not identical to the surrounding tissue. The use of the microalgal culture supernatant of the invention can prevent or reduce the formation of scar or reduce the unpleasant appearance of the scar tissue formed during the process of healing.

The invention also relates to the pharmaceutical composition of the invention for use in the prevention and/or treatment of a disease or condition which requires increased proliferation of fibroblasts and wherein said treatment is performed in the presence of reduced levels of serum or growth factors. In a preferred embodiment, the disease or condition which requires increased proliferation is selected from the group consisting of periodontal disease, a cutaneous ulcer and a skin scar.

Alternatively, the invention relates to the use of a pharmaceutical composition or combination of the invention for the preparation of a medicament for use in the prevention and/or treatment of a disease or condition which requires increased proliferation of fibroblasts and wherein said treatment is performed in the presence of reduced levels of serum or growth factors.

Alternatively, the invention relates to a method for use in the prevention and/or treatment of a disease or condition which requires increased proliferation of fibroblasts which comprises administering a pharmaceutical composition or a combination of the invention to a subject in need thereof wherein said treatment is performed in the presence of reduced levels of serum or growth factors.

"Reduced amount of fetal serum or growth factors", as used herein relates to a content of serum or growth factors in the media or in the pharmaceutical composition preferably lower than 10%, more preferably 8%, 7%, 6%, 5%, 4%, 3%, 2%, 1% or more preferably 0.5% (v/v).

The pharmaceutical composition of the invention for use in the medical treatments of the invention should be administered in a pharmaceutical effective amount.

The expression "pharmaceutical effective amount", as used herein, is understood as an amount capable of providing a therapeutic effect, and which can be determined by the person skilled in the art by commonly used means. The amount of the combination of the invention or the pharmaceutical compositions according to the invention will vary depending upon the subject and the particular mode of administration. Those skilled in the art will appreciate that dosages may also be determined with guidance from Goodman and Goldman's The Pharmacological Basis of Therapeutics, Ninth Edition (1996), Appendix II, pp. 1707-1711 and from Goodman and Goldman's The Pharmacological Basis of Therapeutics, Tenth Edition (2001), Appendix II, pp. 475-493.

The appropriate dosage of the active principle or principles within the combination or pharmaceutical composition will depend on the type of disease to be treated, the severity and course of the disease, whether the composition is administered for preventive or therapeutic purposes, previous therapy, the patient's clinical history and response to the peptide or polypeptide, and the discretion of the attending physician. The amount of the combination of the invention or the pharmaceutical compositions according to the invention is suitably administered to the patient at one time or over a series of treatments. Depending on the type and severity of the disease, an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

If desired, the combination, the pharmaceutical or cosmetic composition of the invention is incorporated in a fabric, a non-woven fabric or a medical device. Illustrative examples of said fabric, non-woven fabric or medical device include but are not limited to bandages, gauzes, t-shirts, panty hose, socks, underwear, girdles, gloves, diapers, sanitary napkins, dressings, bedspreads, towelettes, adhesive patches, non-adhesive patches, occlusive patches, microelectric patches and face masks.

Where necessary, the combination, the pharmaceutical or cosmetic composition is comprised in a composition also including a solubilizing agent and a local anesthetic to ameliorate any pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the combination, the pharmaceutical or cosmetic composition is to be administered by infusion, it can be dispensed with an infusion bottle containing sterile pharmaceutical grade water or saline. Where the composition is administered by injection, an ampule of sterile water for injection or saline can be provided so that the ingredients may be mixed prior to administration.

In cases other than intravenous administration, the combination, the pharmaceutical or cosmetic composition can contain minor amounts of wetting or emulsifying agents, or pH buffering agents. The composition can be a liquid solution, suspension, emulsion, gel, polymer, or sustained release formulation. The composition can be formulated with traditional binders and carriers, as would be known in the art. Formulations can include standard carriers such as pharmaceutical grades of mannitol, lactose, starch, magnesium stearate, sodium saccharide, cellulose, magnesium carbonate, etc., inert carriers having well established functionality in the manufacture of pharmaceuticals. Various delivery systems are known and can be used to administer a combination or pharmaceutical composition of the present invention including encapsulation in liposomes, micropar-ticles, microcapsules and the like.

Solid dosage forms for oral administration may include conventional capsules, sustained release capsules, conventional tablets, sustained-release tablets, chewable tablets, sublingual tablets, effervescent tablets, pills, suspensions, powders, granules and gels. At these solid dosage forms, the active compounds can be mixed with at least one inert excipient such as sucrose, lactose or starch. Such dosage forms can also comprise, as in normal practice, additional substances other than inert diluents, e.g. lubricating agents such as magnesium stearate. In the case of capsules, tablets, effervescent tablets and pills, the dosage forms may also comprise buffering agents. Tablets and pills can be prepared with enteric coatings.

Liquid dosage forms for oral administration may include emulsions, solutions, suspensions, syrups and elixirs pharmaceutically acceptable containing inert diluents commonly used in the technique, such as water. Those compositions may also comprise adjuvants such as wetting agents, emulsifying and suspending agents, and sweetening agents, flavoring and perfuming agents.

Injectable preparations, for example, aqueous or oleaginous suspensions, sterile injectable may be formulated according with the technique known using suitable dispersing agents, wetting agents and/or suspending agents. Among the acceptable vehicles and solvents that can be used are water, Ringer's solution and isotonic sodium chloride solution. Sterile oils are also conventionally used as solvents or suspending media.

For topical administration the combination, the pharmaceutical or cosmetic composition of the invention can be formulated as creams, gels, lotions, liquids, pomades, spray solutions, dispersions, solid bars, emulsions, microemulsions and similars which may be formulated according to conventional methods that use suitable excipients, such as, for example, emulsifiers, surfactants, thickening agents, coloring agents and combinations of two or more thereof.

Additionally, the combination, the pharmaceutical or cosmetic composition of the invention may be administered in the form of transdermal patches or iontophoresis devices. In one embodiment, the combination of the invention is administered as a transdermal patch, for example, in the form of sustained-release transdermal patch. Suitable transdermal patches are known in the art.

In some embodiments, the therapeutic composition can be added to suitable contact layer dressings, including, for example, thin, non-adherent sheets placed on an area to protect tissue from for example, direct contact with other agents or dressings applied to the treatment site. In some embodiments, contact layers can be deployed to conform to the shape of the area of the skin treatment site and are porous to allow the skin augmentation composition to pass through for absorption onto the skin treatment site.

Elastic Bandages: suitable elastic bandages can include dressings that stretch and conform to the body contours. In certain embodiment, the fabric composition can include for example, cotton, polyester, rayon or nylon. In certain other embodiments, the elastic bandage can for example, provide absorption as a second layer or dressing, to hold a cover in place, to apply pressure or to cushion a treatment site.

Foams: suitable foam dressings can include sheets and other shapes of foamed polymer solutions (including polyurethane) with small, open cells capable of holding liquid solution of the skin augmentation composition. Exemplary foams can be for example, impregnated or layered in combination with other materials. In certain embodiment, the absorption capability can be adjusted based on the thickness and composition of the foam. In certain other embodiments, the area in contact with the treatment site can be non-adhesive for easy removal. In yet another embodiment, the foam can be used in combination with an adhesive border and/or a transparent film coating that can serve as an anti-infective barrier.

Gauzes Non-Woven dressings: suitable gauze dressings and woven dressings can include, dry woven or non-woven sponges and wraps with varying degrees of absorbency. Exemplary fabric composition can include cotton, polyester or rayon. In certain embodiments, gauzes and non-woven dressing can be available sterile or non-sterile in bulk and with or without an adhesive border. Exemplary gauze dressings and woven dressings can be used for moderate to slow release of the skin augmentation composition and covering a variety of wound treatment sites.

Hydrogels (Amorphous): suitable amorphous hydrogel dressings can include formulations of water, polymers and other ingredients with no shape, designed to donate moisture and to maintain a moist healing environments and or to rehydrate the skin treatment site while concomitantly releasing a therapeutically effective amount of the skin augmentation composition. In some embodiments, hydrogels can be used in combination with a secondary dressing cover.

Hydrogel Impregnated Dressings: suitable impregnated hydrogel dressings can include gauzes and non-woven sponges, ropes and strips saturated with an amorphous hydrogel. Amorphous hydrogels can include for example, formulations of water, polymers and other ingredients with no shape, designed to donate moisture to a dry treatment site and to maintain a moist healing environment while concomitantly releasing a therapeutically effective amount of the skin augmentation composition.

Hydrogel Sheets: suitable hydrogel sheets can include for example, three-dimensional networks of cross-linked hydrophilic polymers that are insoluble in water and interact with aqueous solutions by swelling. Exemplary hydrogels are highly conformable and permeable and can release varying amounts of the skin augmentation composition depending on their composition. In some embodiments, the hydrogel is non-adhesive against the skin treatment site or treated for easy removal. The released rate of the skin augmentation composition from the hydrogel can be adjusted depending on the chemical affinity of the hydrogel for the composition. Generally, the released composition provides an amount of each active agent in the range of about 0.01 mg/cm$^2$ to about 10 mg/cm$^2$ of skin treated.

Several drug delivery systems are known and can be used to administer the combinations, pharmaceutical compositions, cosmetic compositions of the invention, including, for example, encapsulation in liposomes, microbubbles, emulsions, microparticles, microcapsules and similars. The required dosage can be administered as a single unit or in a sustained release form.

Sustainable-release forms and appropriate materials and methods for their preparation are described in, for example, "Modified-Release Drug Delivery Technology", Rathbone, M. J. Hadgraft, J. and Roberts, M. S. (eds.), Marcel Dekker, Inc., New York (2002), "Handbook of Pharmaceutical Controlled Release Technology", Wise, D. L. (ed.), Marcel Dekker, Inc. New York, (2000). In one embodiment of the invention, the orally administrable form of a combination or pharmaceutical composition of the invention is in a sustained release form further comprises at least one coating or matrix. The coating or sustained release matrix include, without limitation, natural polymers, semisynthetic or synthetic water-insoluble, modified, waxes, fats, fatty alcohols, fatty acids, natural semisynthetic or synthetic plasticizers, or a combination of two or more of them.

Enteric coatings may be applied using conventional processes known to experts in the art, as described in, for example, Johnson, J. L., "Pharmaceutical tablet coating", Coatings Technology Handbook (Second Edition), Satas, D. and Tracton, A. A. (eds), Marcel Dekker, Inc. New York, (2001), Carstensen, T., "Coating Tablets in Advanced Pharmaceutical Solids", Swarbrick, J. (ed.), Marcel Dekker, Inc. New York (2001), 455-468.

Method for Inducing Fibroblasts Proliferation

The inventors have observed that culture supernatants of the invention have fibroblasts proliferation activity.

Therefore, in another aspect, the invention relates to a method for inducing fibroblast proliferation which comprises contacting a preparation comprising fibroblast with a microalgae culture supernatant according to the invention in the presence of reduced amounts of fetal serum or growth factor. In a preferred embodiment, the method for inducing fibroblast proliferation is an in vitro method.

"Reduced amount of fetal serum or growth factors", as used herein relates to a content of serum or growth factor in the media preferably lower than 10%, more preferably 8%, 7%, 6%, 5%, 4%, 3%, 2%, 1% or more preferably 0.5% (v/v).

All the terms and embodiments previously described are equally applicable to this aspect of the invention.

The following examples illustrate the invention and must not be considered as limiting the same.

EXAMPLES

Example 1: Centrifugation and Lyophilization

*Chlamydomonas* CC-124 (*chlamydomonas* center), UVM4 (Neupert et al. 2009) or any other cell wall less strain (cw15 or CC-1883) was grown mixotrophically in TAP media under continuous light (100 µE), at a constant temperature of 25 C until reaching a stationary phase. *Chlorella protothecoides* was grown in Bold's Basal Medium (BBM) and *Isochrysis galbana* in Guillard F/2 media under same conditions as described above. In order to obtain a cell free enriched media, culture was centrifuged 4000 g for 10 min. to obtain a cell-free supernatant that was concentrated at least 50-fold by lyophilization followed by resuspension in mQH2O. Concentrated supernatant was dialyzed against phosphate buffered saline 1000 times the volume of the sample. A second centrifugation (3000 g for 5 min.) was performed to remove particle aggregates and cell debris. Supernatant is filter sterilized before use with a 0.22 µm nylon filter.

Example 2: Centrifugation and Tangential Flow Filtration

Cells can be grown under same conditions as stated above and supernatant can be concentrated by tangential flow filtration using and ultrafiltration membrane, hollow fiber filtration systems, or a centrifugal device. For concentration, once concentrated a centrifugation is performed to remove particle aggregates and cell debris (4000 g 5'). Supernatant solution is filter sterilized before use with a 0.22 µm nylon filter.

Example 3. IMAC-Enriched Microalga Culture Supernatant

Microalgal culture supernatant containing histidine clusters can be further purified by IMAC. IMAC-enriched microalgal culture supernatant were obtained as follows. UVM4 or CC-124 *Chlamydomonas* strains were grown until an $OD_{750\ nm}$ of 2.5 under same conditions as described in Example 1. Once culture reached late phase of growth, supernatant was separated from cells by the addition of 0.005% Tween20 followed by centrifugation at 4000 g 10', concentration 40× by lyophilization and resuspension in mQH2O. Concentrated media was centrifuged at 3000 g 5', applied to 0.5 mL of Nickel Sepharose Excel resin (Nickel sepharose Excel, GE Healthcare) previously equilibrated in Buffer A (50 mM potassium phosphate pH 8, 0.3 M NaCl, 0.1% Triton X-100), and incubated under slow rotation at 4 C for 4 h. Resin bound proteins were washed 5 times with 10 volumes each of Buffer A. Molecules were eluted by incubating resin with 5 mL Elution buffer (50 mM potassium phosphate, 0.3 M NaCl, 0.1% Triton X-100, 0.5M imidazol). Concentration and diafiltration of eluted fraction was performed to obtain a final 2 ml eluate in 50 mM potassium phosphate pH8, 50 mM NaCl. BSA was added to the purified fraction at final concentration of 0.1% (w/v)

Example 4 MTT Assay to Determine Cell Viability of Fibroblasts

Microalgal culture supernatant from *Chlamydomonas* strains (CC-124, CC-1690, CC-1691, cw15 and UVM4), *Chlorella protothecoides* or *Isochrysis galbana* were obtained as described in Example 1, or UVM4 or CC 124 IMAC-enriched microalgal culture supernatant obtained as described in Example 3 were added to NIH3T3 cells growing in DMEM+0.5% FBS. Proliferation of fibroblasts (NIH3T3 or BALB3T3) induced by different microalgal culture supernatants or IMAC-enriched microalgal culture supernatant fractions were measured by MTT assays. NIH3T3/BALB3T3. fibroblasts were cultivated in DMEM media+10% fetal bovine serum (FBS). Culture was maintained at 37 C with 5% CO2 and 90% humidity. All assays were performed with cells at 90% confluence and viability greater than 90%. 10000 cells were seed in 96 well plates coated with 1% gelatin in 100 µl of complete media (DMEM+10% FCS). After 24 h, cells were washed with DMEM and new DMEM+0.5% FBS with different dilutions of IMAC enriched microalgal culture supernatant (IE-MS) or EGF was added. After 72 hours of incubation in the different supplemented media, this was replaced with new media containing 10 µl MTT (5 mg/ml dissolved in PBS) and incubated for 3 h at 37 C. After that, MTT containing media was removed, extraction buffer was added (50% dimetilformamide, 15% SDS) and incubated for 1 h at 37 C. Values from wells with 0% viability (treatment with 2.5% TritonX-100) was considered background signal. Absorbance was measured at 570 nm with Multiskan Ascent microplate reader. For normalization, viability of cells in DMEM-0.5% FBS was set at 100%

Figure 2:
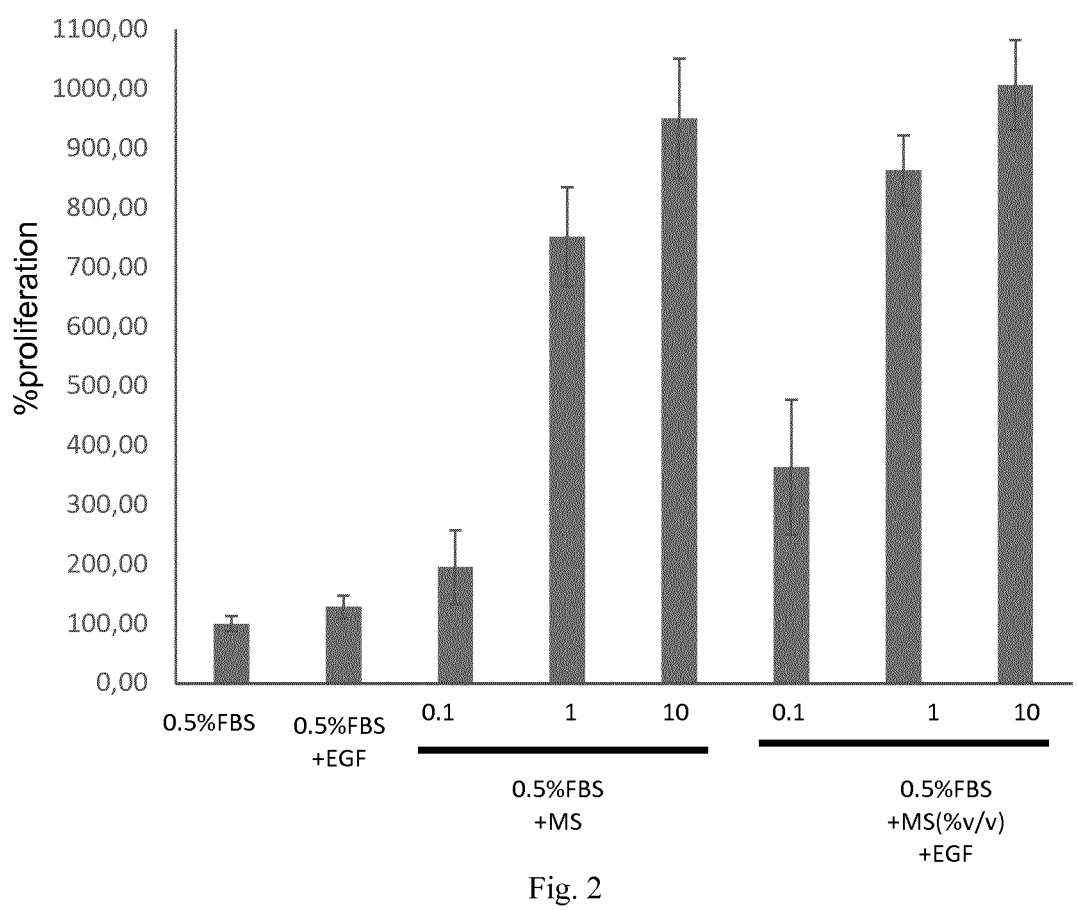
FIG. 2: Effect of microalgal culture supernatant on fibroblast proliferation. NIH3T3 cells were cultivated in the presence of basal DMEM media containing 0.5% fetal Bovine Serum. Proliferation was compared to culture containing different concentrations of microalgal culture supernatant (MS) (% v/v referred to final volume from a *Chlamydomonas* cell free media that has been 53× concentrated) in the presence or absence of human recombinant EGF. Cell media that was previously concentrated 53× (by liophyllization) and dyalized against PBS was added to a final concentration ranging from 0.1% to 10% of total cell culture volume. (e.g. 2, 20 or 20 µL in 200 µL final volume). Cell viability of NIH3T3 fibroblast was determined by MTT assay.
Figure 3:
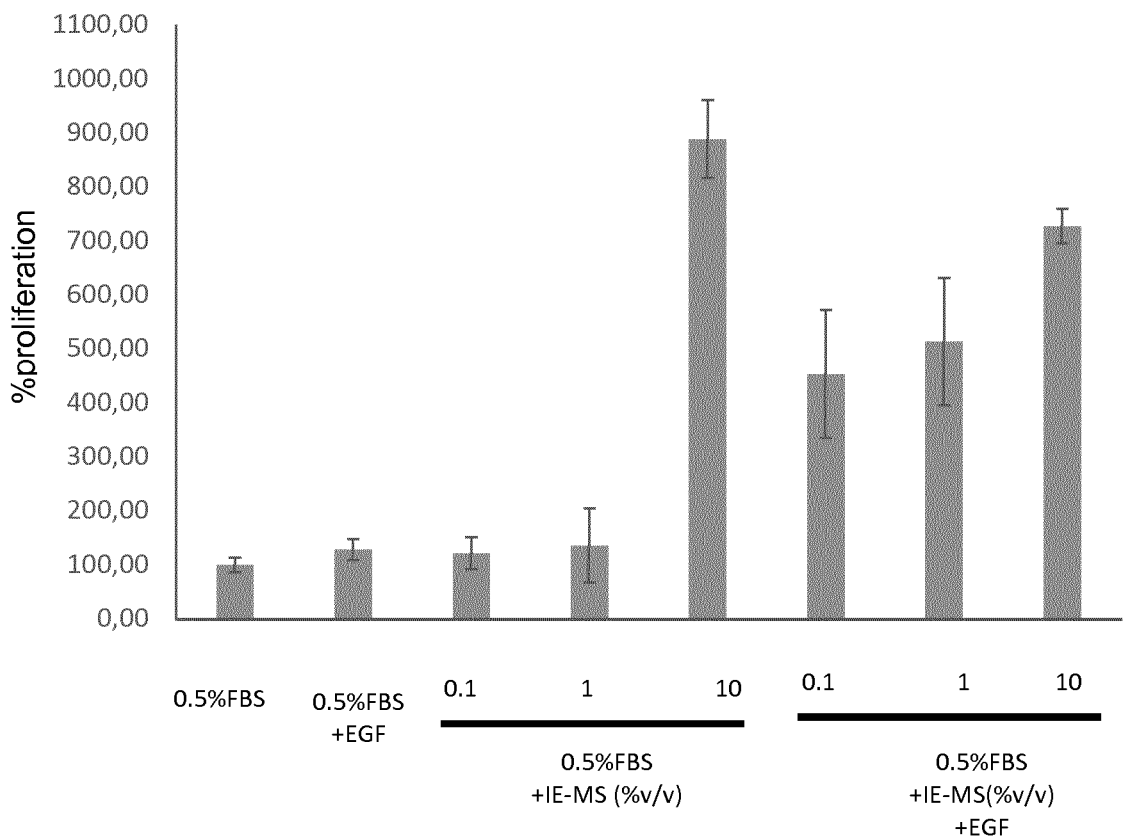
FIG. 3: A. Effect of IMAC-enriched microalgal culture supernatant on fibroblast proliferation. NIH3T3 cells were cultivated in the presence of basal DMEM media containing 0.5% fetal Bovine Serum. Proliferation was compared to culture containing different concentrations of IMAC-enriched microalgal culture supernatant (IE-MS) (% v/v referred to final volume of IMAC-enriched microalga culture supernatant fraction that was enriched 200× referred to volume of culture) in the presence or absence of human recombinant EGF. A 0.1%, 1% or 10% volume of IMAC-enriched microalga culture supernatant fraction (enriched 200× referred to volume of culture) was added to DMEM media (e.g 2, 20 or 20 µL in 200 µL final volume). Cell viability of NIH3T3 fibroblast was determined by MTT assay. B. Effect of concentrated microalgal culture supernatants (MS) on fibroblast proliferation. BALB 3T3 cells were cultivated in the presence of basal DMEM media containing 0.5% fetal Bovine Serum+/−EGF. Proliferation was compared to culture containing different concentrations of microalgal culture supernatant (MS) (% v/v referred to final volume from a microalgae cell free media that has been 53× concentrated by lyophilization and dialyzed against PBS). Concentrated MS was added to a final concentration ranging from 0.1% to 10% of total cell culture volume. (e.g. 2, 20 or 20 µL in 200 µL final volume). Cell viability of BALB3T3 fibroblasts was determined by MTT assay.
Figure 3:
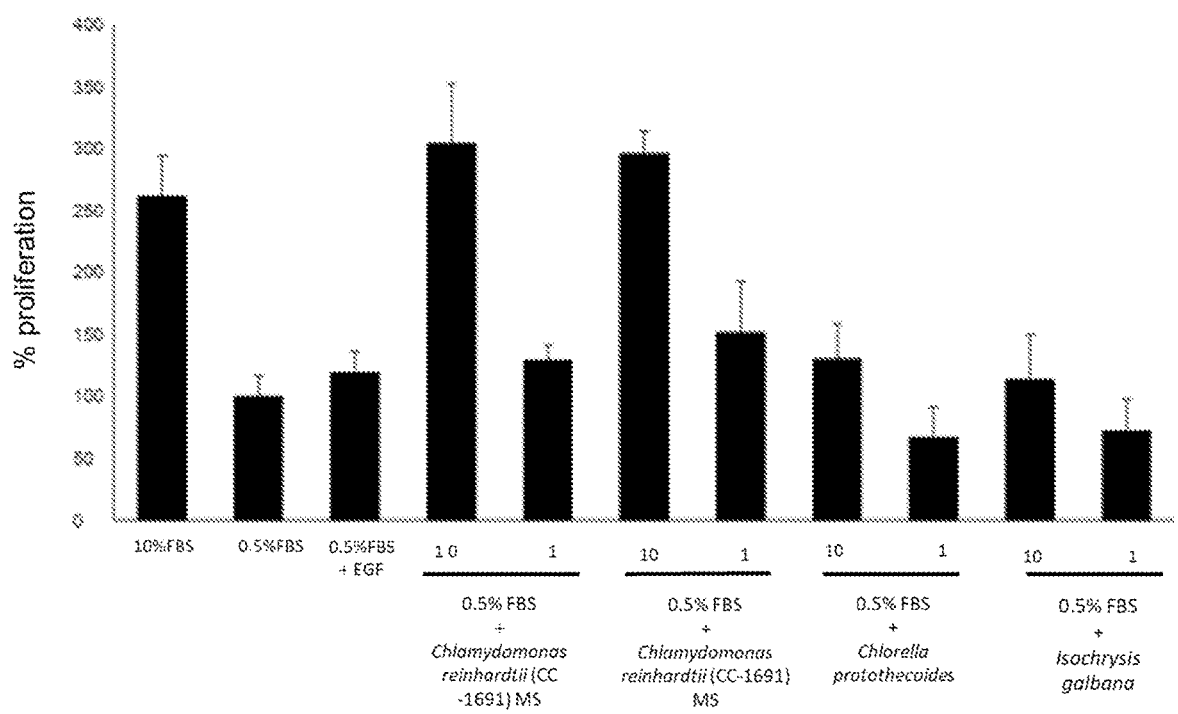

Concentrated glycoprotein rich extract was obtained according to example 1 (50× concentrated compared to initial volume) or example 3 above described (200× concentrated compared to initial culture volume). This preparation contains 2-6 g/L of carbohydrates and 0.1-0.4 mg/L of proteins Example 5 Microalgal Culture Supernatant Effect on Murine Fibroblast Proliferation To determine the effect of microalgal culture supernatant microalga culture supernatant (MS) on fibroblasts proliferation, NIH3T3 cells were cultivated until confluence in DMEM+10% FBS (protocol described above). FBS was washed out and cells were incubated in DMEM-0.5% FBS containing different concentrations of MS obtained as in example 1 (FIG. 2) or Example 3 (FIG. 3) in the presence or absence of hEGF (1 Ong/ml). After 72 hours cell viability was determined by MTT assay: The results show that both lyophilized/dialyzed microalgal culture supernatant (FIG. 2) and IMAC-enriched microalgal culture supernatant (FIG. 3) cause an increase on proliferative activity of fibroblasts in a dose dependent manner. When MS is added at concentration 1 and 0.1% a synergistic effect with EGF is observed. Error bars represent standard deviation of 5 biological replicates.

Figure 4:
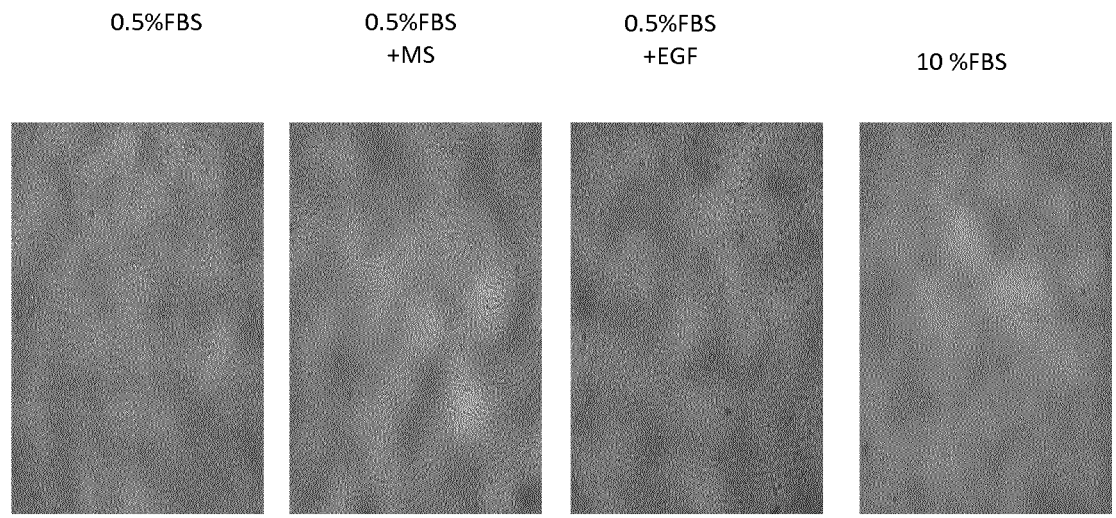
FIG. 4. A. Images of NIH3T3 fibroblasts cultivated for 24 h in DMEM 0.5% FBS, DMEM 0.5% FBS+microalgal culture supernatant (MS), DMEM 0.5% FBS+hEGF (10 ng/ml), DMEM+10% FBS. B. Macroscopic differences observed between the lyophilized concentrated supernatant of different microalgae: A) *Isochrysis galbana*; B) *Chlorella protothecoides*; C) *Chlamydomonas reinhardtii*
Figure 4:
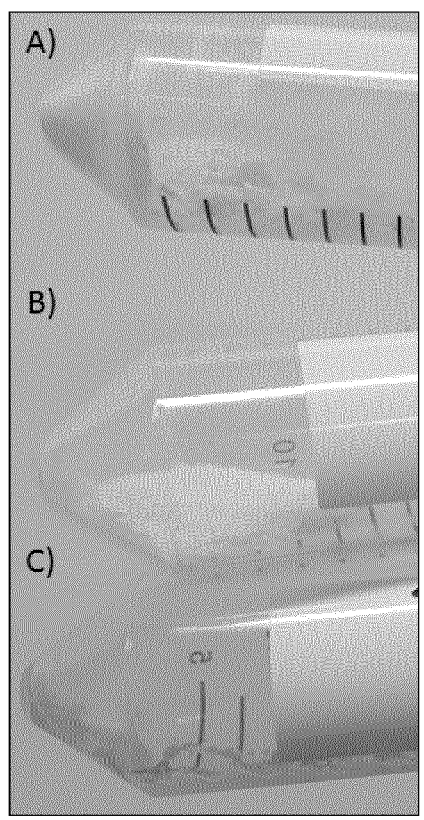

Example 6 Microalgal Culture Supernatant Effect on Murine Fibroblast Organization Organization and proliferation of fibroblasts was compared when cells were grown on DMEM media+0.5% FBS, in the presence of *Chlamydomonas* microalgal culture supernatant (10% from microalgal culture supernatant or in the presence of recombinant EGF). The presence of glycoproteins induced a clear reorganization of fibroblast and visually increased density that was not observed when cultured with EGF (10 ng/ml) or increasing concentrations of FBS (10%) (FIG. 4).

The invention claimed is:

1. A method for wound healing, for repairing skin damage or for the treatment of a disease or condition by increasing proliferation of fibroblasts in a subject in need thereof comprising administering to the subject a pharmaceutical composition comprising a pharmaceutically acceptable adjuvant and
   (i) a microalgal culture supernatant comprising components naturally secreted by microalgae obtained by a method comprising the steps of:
   a) culturing microalgae belonging to Chlorophyceae class or Volvocales order under conditions suitable for a growth of the microalgae and for the secretion of molecules to a culture medium, and
   b) obtaining a microalgal culture supernatant by removing cells from the culture of step a), said cells maintaining the membrane integrity, and
   c) concentrating the microalgal culture supernatant using a membrane with a cut off of at least 10 kDa by tangential flow filtration or by lyophilization followed by dialysis;
   (ii) an IMAC-enriched microalgal culture supernatant comprising components naturally secreted by microalgae obtained by a method comprising the steps of:
   a) culturing microalgae belonging to Chlorophyceae class or Volvocales order under conditions suitable for a growth of the microalgae and for a secretion of molecules to a culture medium,
   b) obtaining a microalgal culture supernatant by removing cells from the culture of step a), said cells maintaining the membrane integrity,
   c) incubating the microalgal culture supernatant from step b) with a metal affinity chromatography resin under conditions allowing a binding of molecules to a resin of the molecules in the supernatant which show affinity to the resin,
   d) separating the molecules that bind to the metal affinity chromatography resin from the molecules that do not bind, and
   e) eluting from the resin the molecules that bind to the resin, thereby obtaining an IMAC-enriched microalga culture supernatant; or
   (iii) a combination comprising a growth factor, and a microalgal culture supernatant as defined in (i) or an IMAC-enriched microalgal culture supernatant as defined in (ii).

2. The method according to claim 1, wherein the treatment is performed in the presence of less than 10% of fetal serum or growth factors.

3. The method according to claim 1, wherein the disease or condition is selected from the group consisting of periodontal disease, a cutaneous ulcer and a skin scar.

4. The method according to claim 1, wherein the microalgae is from Chlorophyceae class.

5. The method according to claim 4, wherein the microalgae from Chlorophyceae class is from Volvocales order.

6. The method according to claim 5, wherein the microalgae from Volvocales order is from Chlamydomonadaceae family.

7. The method according to claim 6, wherein the microalgae from Chlamydomonadaceae family is from the genus *Chlamydomonas*.

8. The method according to claim 7, wherein the microalgae from the genus *Chlamydomonas* is *C. reinhardtii*.

9. The method according to claim 1, wherein the microalgae is from a cell wall-less strain.

10. The method according to claim 9, wherein the strain is UVM4, CC-124, cw15 or CC-1883.

11. The method according to claim 1, wherein the removing of the cells in step (i)b) and (ii)b) is performed by centrifugation.

12. The method according to claim 1, wherein the IMAC-enriched microalgal culture supernatant of step d) is further concentrated.

13. The method according to claim 12, wherein the concentration is performed by lyophilization or by tangential flow filtration.

14. The method according to claim 1, wherein the microalgae is grown under mixotrophic conditions.

15. The method according to claim 1, wherein the growth factor is EGF.

16. A cosmetic method for skin care comprising administrating to a subject in need there of a cosmetic composition or cosmeceutical comprising a cosmetically acceptable adjuvant and
  (i) a microalgal culture supernatant comprising components naturally secreted by microalgae obtained by a method comprising the steps of:
    a) culturing microalgae belonging to Chlorophyceae class or Volvocales order under conditions suitable for the growth of the microalgae and for a secretion of molecules to a culture medium, and
    b) obtaining a microalgal culture supernatant by removing cells from the culture of step a), said cells maintaining the membrane integrity; and
    c) concentrating the microalgal culture supernatant using a membrane with a cut off of at least 10 kDa by tangential flow filtration or by lyophilization followed by dialysis;
  (ii) an IMAC-enriched microalgal culture supernatant comprising components naturally secreted by microalgae obtained by a method comprising the steps of:
    a) culturing microalgae belonging to Chlorophyceae class or Volvocales order under conditions suitable for the growth of the microalgae and for a secretion of molecules to a culture medium,
    b) obtaining a microalgal culture supernatant by removing cells from the culture of step a), said cells maintaining the membrane integrity,
    c) incubating the microalgal culture supernatant from step b) with a metal affinity chromatography resin under conditions allowing a binding of the molecules in the supernatant showing affinity to a resin,
    d) separating the molecules that bind to the metal affinity chromatography resin from the molecules that do not bind, and
    e) eluting from the resin the molecules that bind to the resin, thereby obtaining an IMAC-enriched microalga culture supernatant; or
  (iii) a combination comprising a growth factor, and a microalgal culture supernatant as defined in (i) or an IMAC-enriched microalgal culture supernatant as defined in (ii), wherein the method treats a condition by increasing proliferation of fibroblasts.

17. The cosmetic method according to claim 16, wherein the cosmetic method treats a condition selected from the group consisting of premature skin aging, chronological aging, photoaging and cutaneous senescence.

* * * * *